(12) United States Patent
Huddart et al.

(10) Patent No.: US 12,023,449 B2
(45) Date of Patent: Jul. 2, 2024

(54) PRESSURE CONTROLLED EXHAUST VENT

(71) Applicant: Fisher & Paykel Healthcare Limited, Auckland (NZ)

(72) Inventors: Brett John Huddart, Auckland (NZ); Andrew Paul Maxwell Salmon, Auckland (NZ); Matthew James Pedersen, Auckland (NZ); Hamish Joshua Rose, Auckland (NZ); Fadi Karim Moh'd Mashal, Auckland (NZ); Thomas Mark Richardson, Auckland (NZ); Simon Mittermeier, Auckland (NZ); Max Leon Betteridge, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 746 days.

(21) Appl. No.: 17/154,782

(22) Filed: Jan. 21, 2021

(65) Prior Publication Data

US 2021/0138183 A1 May 13, 2021

Related U.S. Application Data

(63) Continuation of application No. 15/312,135, filed as application No. PCT/IB2015/053666 on May 19, 2015, now Pat. No. 10,953,190.

(Continued)

(51) Int. Cl.
*A61M 16/20* (2006.01)
*A61M 16/06* (2006.01)
(Continued)

(52) U.S. Cl.
CPC .......... *A61M 16/208* (2013.01); *A61M 16/06* (2013.01); *A61M 16/209* (2014.02);
(Continued)

(58) Field of Classification Search
CPC .. A61M 16/06; A61M 16/08; A61M 16/0816; A61M 16/20; A61M 16/201;
(Continued)

(56) References Cited

U.S. PATENT DOCUMENTS 2,515,073 A * 7/1950 Binnall ................. G05D 7/012
138/45
3,901,272 A * 8/1975 Banners ............... F16K 15/147
137/513.5

(Continued)

FOREIGN PATENT DOCUMENTS

CN 102015000 4/2011
EP 0756881 2/1997

(Continued)

OTHER PUBLICATIONS

International Search Report: PCT/IB2015/053666; dated Jul. 31, 2015; 3 pages.

(Continued)

*Primary Examiner* — Colin W Stuart
*Assistant Examiner* — Douglas Y Sul
(74) *Attorney, Agent, or Firm* — Knobbe, Martens, Olson & Bear, LLP

(57) ABSTRACT

A patient interface includes a mask body, an elbow, a connector and a conduit. Any one or more of the mask body, the elbow, the connector and the conduit includes a bias flow vent. The bias flow vent is configured to deform with the application of pressure but not fully collapse such that an orifice size defined by the bias flow vent can vary with the application of pressure.

21 Claims, 25 Drawing Sheets

Related U.S. Application Data

(60) Provisional application No. 62/000,163, filed on May 19, 2014.

(51) Int. Cl.
*A61M 16/08* (2006.01)
*A61M 16/22* (2006.01)
*F16K 15/14* (2006.01)

(52) U.S. Cl.
CPC ........... *A61M 16/22* (2013.01); *F16K 15/144* (2013.01); *A61M 16/0816* (2013.01); *A61M 2205/42* (2013.01)

(58) Field of Classification Search
CPC .............. A61M 16/208; A61M 16/209; A61M 2205/42; F16K 15/147; F16K 15/1471; F16K 15/1472; F16K 15/144; F16K 15/145; G05D 7/0106; G05D 7/0113; Y10T 137/7895
USPC .................................................... 137/45, 859
See application file for complete search history.

(56) References Cited

U.S. PATENT DOCUMENTS

| | | | |
|---|---|---|---|
| 4,414,973 A | 11/1983 | Matheson et al. | |
| 4,457,343 A * | 7/1984 | Zukausky | G05D 7/012 239/533.14 |
| 5,027,823 A * | 7/1991 | Sanaka | A61B 5/0235 137/513.5 |
| 5,137,024 A * | 8/1992 | Souma | A61B 5/0235 137/513.5 |
| 5,881,772 A | 3/1999 | Bennett | |
| 6,581,594 B1 | 6/2003 | Drew | |
| 2002/0195108 A1 | 12/2002 | Mittelstadt | |
| 2003/0000532 A1 | 1/2003 | Bowman et al. | |
| 2006/0266361 A1 | 11/2006 | Hernandez | |
| 2009/0050156 A1 | 2/2009 | Ng | |
| 2009/0308398 A1* | 12/2009 | Ferdinand | A61M 15/085 128/207.18 |
| 2010/0262073 A1 | 10/2010 | Henniges | |
| 2011/0240030 A1* | 10/2011 | Ho | A61M 16/0825 128/206.21 |
| 2012/0132209 A1 | 5/2012 | Rummery et al. | |
| 2012/0192870 A1 | 8/2012 | Dugan et al. | |
| 2014/0283831 A1* | 9/2014 | Foote | A61B 5/087 128/204.19 |

FOREIGN PATENT DOCUMENTS

| | | | | |
|---|---|---|---|---|
| WO | WO 2003/000329 | | 1/2003 | |
| WO | WO-03000329 A3 * | | 4/2003 | ........ A61M 15/0015 |
| WO | WO 2013/067592 | | 5/2013 | |

OTHER PUBLICATIONS

Chinese First Office Action; dated May 31, 2018; 13 pages.
European Office Action for Appl. No. 15796260.6 dated Aug. 10, 2018 in 5 pages.
Examination Report of Australian Appl. No. 2015262953 dated Feb. 1, 2019 in 4 pages.

* cited by examiner

PRESSURE CONTROLLED EXHAUST VENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to bias flow vents for use in CPAP systems. More particularly, the present invention relates to such vents that are arranged and configured to regulate bias flow such that it is relatively constant over a wide range of operating pressures.

Description of the Related Art

The treatment of obstructive sleep apnoea (OSA) by continuous positive airway pressure (CPAP) flow generator systems involves the continuous delivery of pressurized air to the airways of a human via a conduit and an interface (for example, a mask). Typically, the interface creates at least a substantial "seal" on or around the nose and/or the mouth. As the patient exhales, carbon dioxide gas can progressively collect in the delivery system. If left unchecked over a period of time, the accumulation of carbon dioxide can have adverse consequences.

SUMMARY OF THE INVENTION

One solution to the accumulation of carbon dioxide is to provide a washout vent. The washout vent can be provided within the mask system. The washout vent enables a flow of gas to be constantly exhausted to the atmosphere. The constant exhaust flow provides a mechanism to continually remove carbon dioxide, which counters the increase in carbon dioxide level.

The washout vents, while providing a mechanism for removing carbon dioxide, also have a number of trade-offs. State of art practice currently uses a hole/hole array of fixed dimensions. The fixed dimensions have the effect of enabling a bias flow of gas that increases as the CPAP pressure level increases. This increasing flow has implications for a number of parameters that affect the user.

The bias flow exiting through the washout vents typically creates disturbances for the patient and/or the patient's bed partner. The disturbances typically manifest in two forms: noise and draft. Changes in the bias flow rate, which are caused by changes in the CPAP pressure level, directly affect the magnitude of these disturbances. Thus, if a pressure oscillation exists within the system, then it is possible to produce an oscillating disturbance.

The flow and humidity source (for example, blower and humidifier) also can be impacted. Increasing the bias flow results in an increase in the physical dimension and power consumption to cater to the peak flow demand (that is, the sum of patient requirements and the maximum bias flow at peak pressure).

The creation of practical and not so practical solutions to this has been the subject of considerable development efforts. Yet, there is room for continued improvement in resolving the problems associated with reducing or eliminating the accumulation of carbon dioxide within a CPAP system.

Certain aspects relate to a patient interface. The patient interface has a body portion sized and shaped to surround a nose and/or a mouth of a user and adapted to create at least a substantial seal with a face of the user. The patient interface also has a coupling that permits the patient interface to be coupled to a gas delivery system. The patient interface further has a vent that allows passage of gas from an interior of the body portion of a mask to an exterior of the body portion of the mask wherein a portion of the vent comprises means to regulate a flow of gas based on the applied pressure.

In some configurations, the means to regulate flow comprises an orifice constructed with varying wall section thickness.

In some configurations, the wall section thickness varies in the range of 50 to 400 microns.

In some configurations, the means to regulate flow operates in a pressure range of 1 cmH20 to 40 cmH20.

In some configurations, the means to regulate flow occurs without a deformable orifice entirely collapsing.

In some configurations, the means to regulate flow comprises one or more lobes formed by one or more surfaces and the means to regulate occurs without the one or more surfaces coming into contact with itself or themselves.

Certain aspects relate to a valve for use with system for delivering CPAP therapy. The valve comprises a base and a membrane. The membrane has a first end defining an inlet opening. The base has a second end defining an outlet opening. The first end of the membrane has at least one concave portion and at least one convex portion and the first end of the membrane is configured to collapse inwardly to vary a flow path size in response to changes in pressure acting on the membrane.

In some configurations, the at least one concave portion and the at least one convex portion are defined by an inflection on an outer surface of the membrane.

In some configurations, the at least one concave portion and the at least one convex portion are defined by an inflection on an inner surface of the membrane.

In some configurations, the at least one concave portion and the at least one convex portion are defined by a change in membrane thickness.

In some configurations, the at least one concave portion and the at least one convex portion are defined by a change in membrane thickness and an inflection on at least one of an inner surface and an outer surface of the membrane.

In some configurations, the at least one concave portion comprises a lobe and the at least one convex portion comprises a bridging portion.

In some configurations, the valve comprises only two lobes and only two bridging portions.

In some configurations, the valve comprises only three lobes and only three bridging portions.

In some configurations, the valve comprises only four lobes and only four bridging portions.

In some configurations, the valve comprises a triangular base.

In some configurations, the valve comprises a circular base.

In some configurations, the base can have a first geometric shape and the inlet opening defined by the membrane can have a second geometric shape. In some such configurations, the first geometric shape is the same as the second geometric shape. In some such configuration, the first geometric shape is triangular and the second geometric shape is triangular. In some such configurations, the first geometric shape is different from the second geometric shape. In some such configurations, the first geometric shape is circular and the second geometric shape is triangular.

In some configurations, the transition between the base and the inlet opening defined by the membrane is non-linear. In some such configurations, the transition is arcuate. In some configurations, the membrane can have a first portion that transitions in a non-linear manner away from the base but symmetrically to the base and a second portion that transitions from the first portion in a non-linear manner to the inlet but non-symmetrically to the base.

In some configurations, the valve further comprises a splint that extends into a mouth defined by the first end of the membrane.

In some configurations, the splint extends from the first end of the membrane to the second end of the base.

In some configurations, the valve further comprises a bias material disposed at the second end of the base.

In some configurations, the bias material comprises a plurality of bias flow holes.

In some configurations, the bias material comprises a diffuser.

In some configurations, a valve array comprises at least two of the valves.

In some configurations, the at least two valves comprise two rows of valves.

In some configurations, the two rows of valves are nested together.

In some configurations, the two rows have valves disposed side by side.

In some configurations, the at least two valves comprise a predetermined pattern of valves.

In some configurations, the valve array is combined with a mask, the valve array being mounted to the mask.

In some configurations, the valve array is disposed on a seal housing of the mask.

In some configurations, the valve array is disposed on a seal of the mask.

In some configurations, the valve array is disposed on a frame of the mask.

In some configurations, the mask comprises an exhaust conduit and the valve array is disposed in the exhaust conduit.

In some configurations, the valve array is combined with an elbow, the valve array being mounted to the elbow.

In some configurations, the valve array is mounted to a cover that is associated with the elbow.

In some configurations, the cover is removable from the elbow.

In some configurations, the valve array is combined with a swivel, the valve array being mounted to the swivel.

The following describes some practical options to improve current designs.

BRIEF DESCRIPTION OF THE DRAWINGS

These and other features, aspects and advantages of the present invention will now be described with reference to the drawings of several preferred embodiments, which embodiments are intended to illustrate and not to limit the invention, and in which figures.

DETAILED DESCRIPTION OF THE PREFERRED EMBODIMENT

As described above, certain features, aspects and advantages of the present invention relate to providing a bias flow that has significant less variance in flow rate over a normal operating pressure range for CPAP systems.

Figure 1:
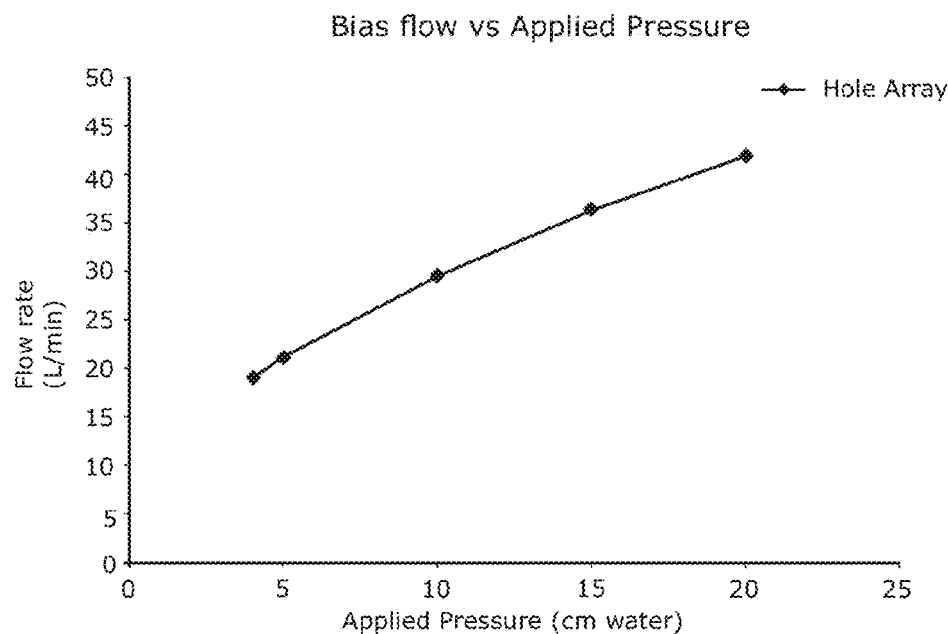
FIG. 1 is a graphical representation of Bias Flow v. Applied Pressure in a system using prior bias flow vent configurations.
Figure 2:
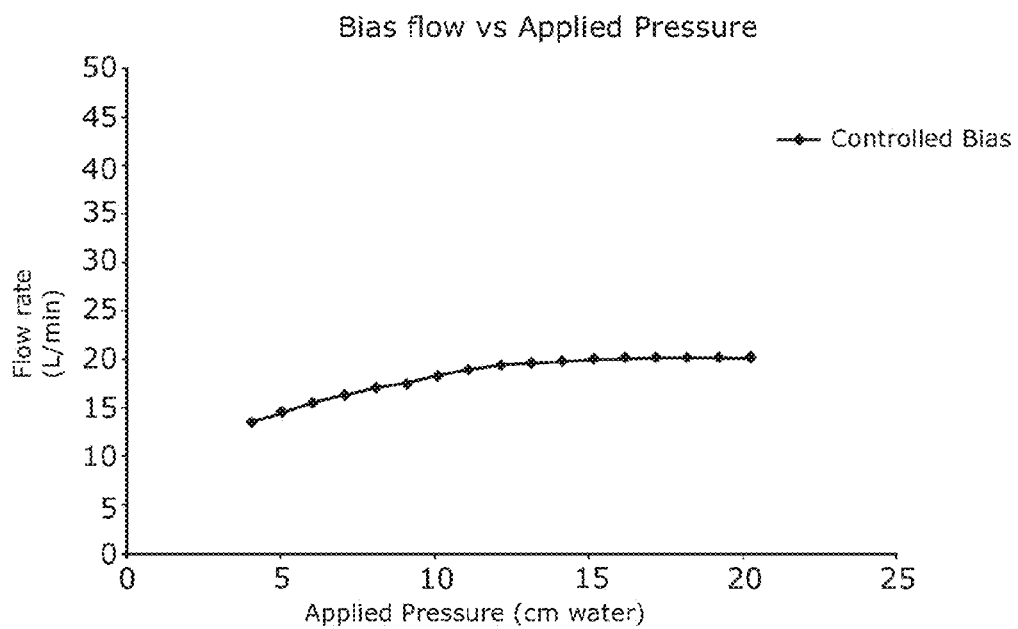
FIG. 2 is a graphical representation of Bias Flow v. Applied Pressure in a system using bias flow vent configurations arranged and configured in accordance with certain features, aspects and advantages of the present invention.

FIG. 1 shows the performance of a conventional bias hole array over a variety of CPAP pressure levels. It can be seen that the bias flow increases by approximately 100% (that is, from about 18 L/min to about 42 L/min) as the pressure is increased from 4 cmH20 to 20 cmH20. FIG. 2 shows the performance of one embodiment of a constant bias flow control system arranged and configured in accordance with certain features, aspects and advantages of the present invention. The illustrated performance is under varying CPAP levels. It can be seen that the bias flow increases by approximately 40% (that is, from about 13 L/min to about 20 L/min) as the pressure is increased from 4 cmH20 to 20 cmH20.

As shown by comparing FIG. 1 and FIG. 2, the constant bias flow control systems that are arranged and configured in accordance with certain features, aspects and advantages of the present invention enable enhanced control over the sound intensity and/or the drafts created as the bias flow exits the CPAP system. Furthermore, the illustrated constant bias flow control systems reduce the flow overhead required in the flow source/CPAP source to accommodate the phenomenon shown in FIG. 1. Because the flow source/CPAP must make up for the ever increasing flow that simply exits through the bias flow vents, the flow source/CPAP size and energy requirement of the flow source/CPAP source must be increased relative to an ideally sized unit.

Valve Geometry

Figure 3:
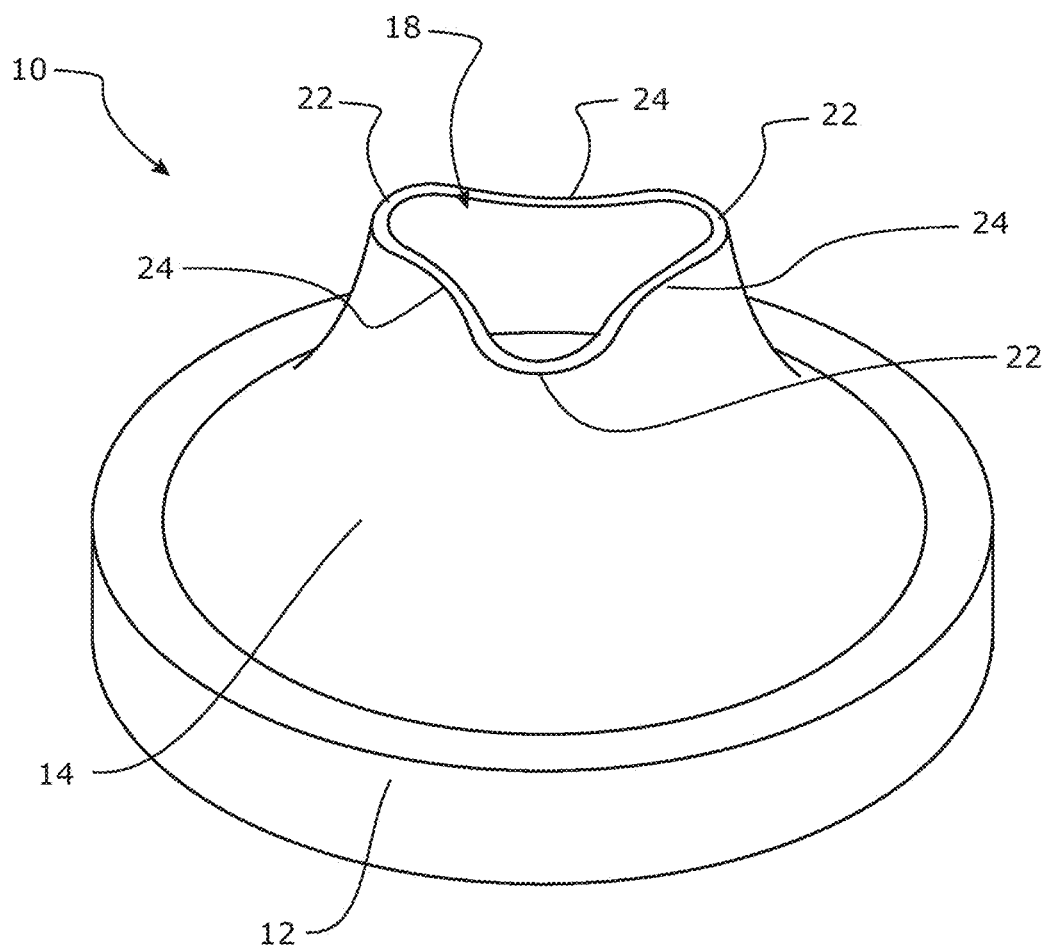
FIG. 3 is a perspective view of a bias flow valve arranged and configured in accordance with certain features, aspects and advantages of the present invention.

FIG. 3 illustrates a bias flow control valve 10 that is arranged and configured in accordance with certain features, aspects and advantages of the present invention. The bias flow control valve 10 advantageously alters the flow opening over a range of pressures. In other words, as the pressure in the system increases, an outlet for gases defined by the bias flow control valve 10 constricts, thereby acting to reduce the bias flow as compared to prior bias flow constructions.

In some configurations, the valve 10 may be formed of silicone rubber (or other suitable thermoplastic elastomers). Silicone contains hydrophobic characteristics that are beneficial for reducing or eliminating condensation build up in or on the valve 10 during use. Any other suitable material or combination of materials can be used. In some configurations, a less flexible portion of the valve 10 may be formed of a first material and a more flexible portion of the valve 10 may be formed of a second, less resilient, material when compared to the first material.

Figure 7:
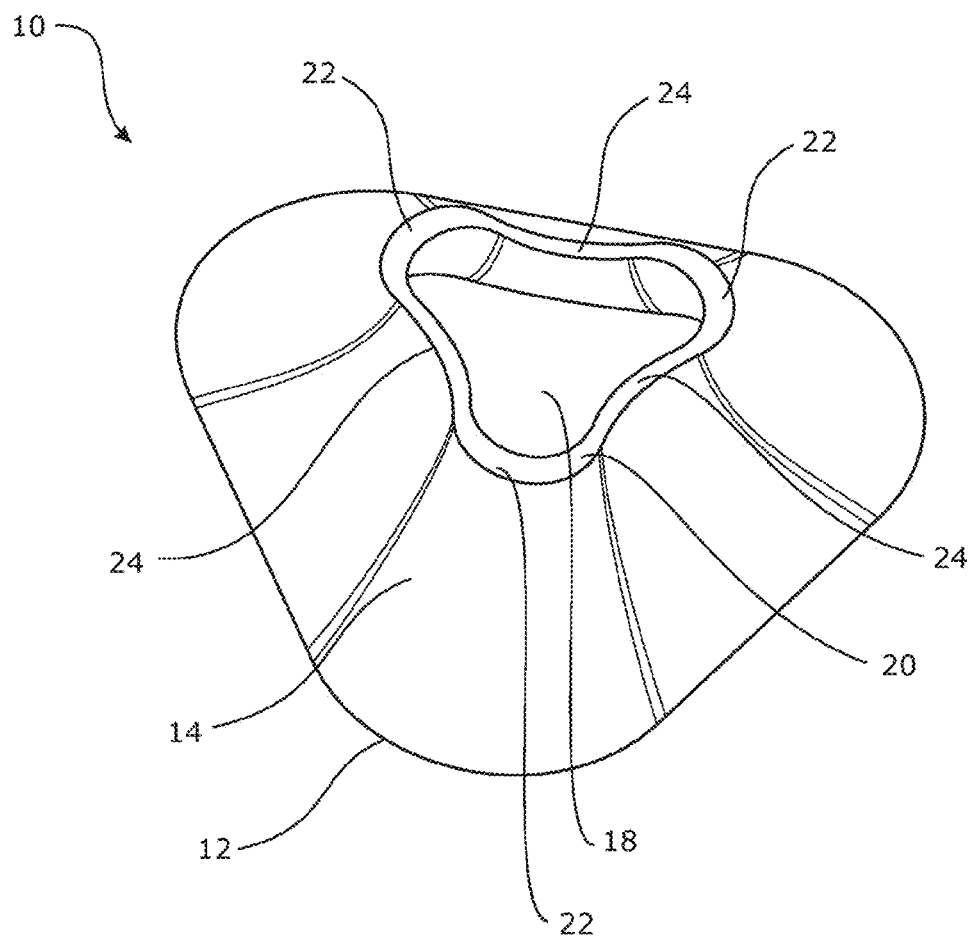
FIG. 7 is a perspective view of a bias flow valve arranged and configured in accordance with certain features, aspects and advantages of the present invention.

The illustrated bias flow control valve 10 comprises a base 12. The base 12 can include a flange or a rim. In the arrangement of FIG. 3, for example, the base 12 is ring-like and can define an outer ring. In other words, in the arrangement of FIG. 3, the base is generally circular in configuration. As shown in FIG. 7, the base 12 does not have to be circular but can have any other desired shape. In some configurations, the base 12 can be a smooth, non-circular or non-cylindrical shape, such as the triangular shape of FIG. 7. The shape of the base can vary from configuration to configuration. By varying the shape of the base, different geometries of surrounding structures can be accommodated. In some configurations, multiple valves are used and, by having the base 12 have a triangular shape, for example but without limitation, an increased number of valves 10 can be mounted over a predetermined surface area. The shape of the base 12 can vary between two or more valves in a single multi-valve configuration or the shape of the base 12 can be consistent between all valves in a single multi-valve configuration.

The base 12 facilitates coupling or connection to the component to which the bias flow control valve 10 is mounted. Any suitable configuration can be used keeping in mind a desire to join the valve 10 to the component in or to which it is mounted. In some configurations, the valve 10 is not removable from the component in or to which it is mounted without significant destruction to the valve 10 and/or the component. In some such configurations, the base 12 forms an integral portion with a surrounding structure.

Figure 5:
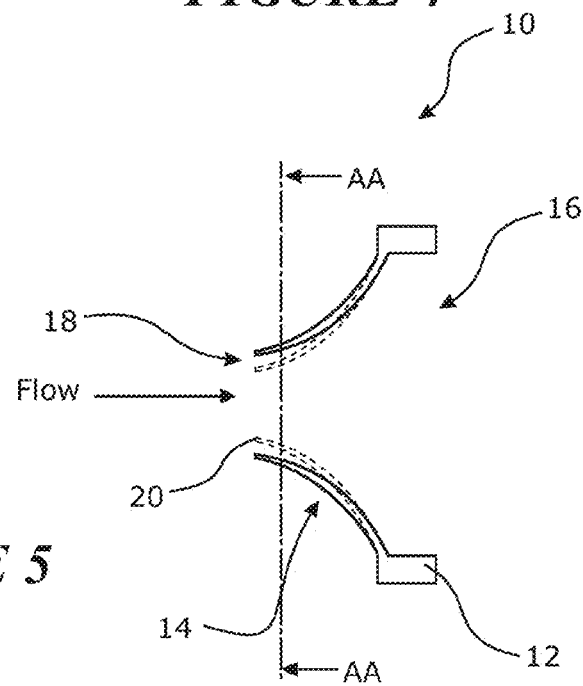
FIG. 5 is a schematic sectioned view of the bias flow valve of FIG. 3.

A membrane 14 can be connected to the base 12 in any suitable manner. In some configurations, the membrane 14 can be integrally formed with the base 12. The membrane 14 is relatively more flexible than the base 12. With reference to FIG. 5, in the illustrated configuration, an outlet 16 can be defined by the base 12 and an inlet 18 can be defined by the membrane 14. The inlet 18 and the outlet 16 are axially offset from each other in the direction of flow (that is, along the central axis of the valve 10). In some configurations, the inlet 18 and the outlet 16 can be axially offset by different distances at different operating pressures. In some configurations, the inlet 18 moves toward the outlet 16 as pressure within the system increases.

In some configurations, such as shown in FIG. 3, the base 12 and the inlet 18 defined by the membrane 14 can have different geometries (for example, a circular base 12 with a triangular inlet 18). In some configurations, such as shown in FIG. 7, the base 12 and the inlet 18 can have similar geometries (for example, a triangular base 12 and a triangular inlet 18). In some configurations, the transition between the base 12 and the inlet 18 is non-linear (that is, even when transitioning from a triangular base to a triangular opening, the wall has an arc in cross-section instead of a linear progression). Such a non-linear configuration, for example, can be seen in FIG. 3, FIG. 5, and FIG. 7. In some configurations, the membrane 14 can have a first portion that transitions in a non-linear manner away from the base 12 but symmetrically to the base and a second portion that transitions from the first portion in a non-linear manner to the inlet 18 but non-symmetrically to the base.

In terms of flow path size, the inlet 18 is a first size in a first condition and the inlet 18 is smaller in a second condition. That is, under a first operating pressure in the system, the inlet 18 can have a first size and, under a second operating pressure in the system that is higher than the first operating pressure, the inlet 18 can have a second size that is smaller than the first size. In other words, the outlet 16 can have a first inner perimeter length and the inlet 18 can be defined by a rim 20 formed on the membrane 14 with the inlet 18 having a second inner perimeter length. The second inner perimeter length can be less than the first inner perimeter length. In some configurations, the inlet has an opening with three lobes 22 and an opening area of 18.5 mm2. In such configurations, the valve 10 can be used alone as a single valve and transmit an initial flow of 15 L/min at a CPAP pressure of 5 cmH2O.

As shown in FIG. 5, the inlet 18 is disposed into the direction from which the flow originates. Thus, the membrane 14 is positioned on the higher pressure side of the base 12 in the illustrated configuration. As shown in FIG. 5, at least a portion of the membrane 14 can deflect with the application of pressure (for example, the dotted lines show the deflection of the valve 10). The deflection of the membrane 14 serves to constrict at least a portion of the flow passage through the valve. In the illustrated configuration, the deflection of the membrane 14 serves to constrict the inlet 18 to the valve 10. In some configurations, the membrane 14 deflects in two directions (that is, one or more of the walls surrounding the opening of the inlet 18 deflect inwardly to decrease the flow path through the opening and the inlet 18 moves axially toward the outlet).

Figure 4:
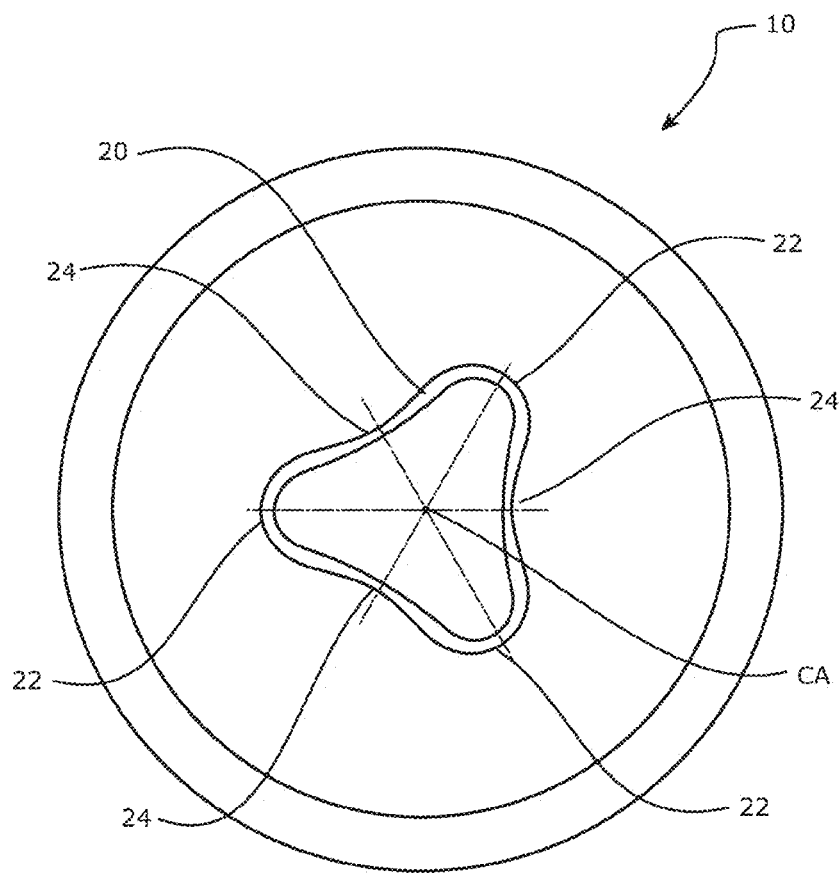
FIG. 4 is a top view of the bias flow valve of FIG. 3.

As shown in FIG. 4, the rim 20 can define two or more lobes 22. Each lobe 22 can be connected to an adjacent lobe 22 with a bridging portion 24. The lobes present themselves as concave regions (that is, concave with respect to the center axis of the passageway defined through the valve 10). The bridging portions 24 can present themselves as convex regions (that is, convex with respect to the center axis of the passageway defined through the valve 10).

Figure 10:
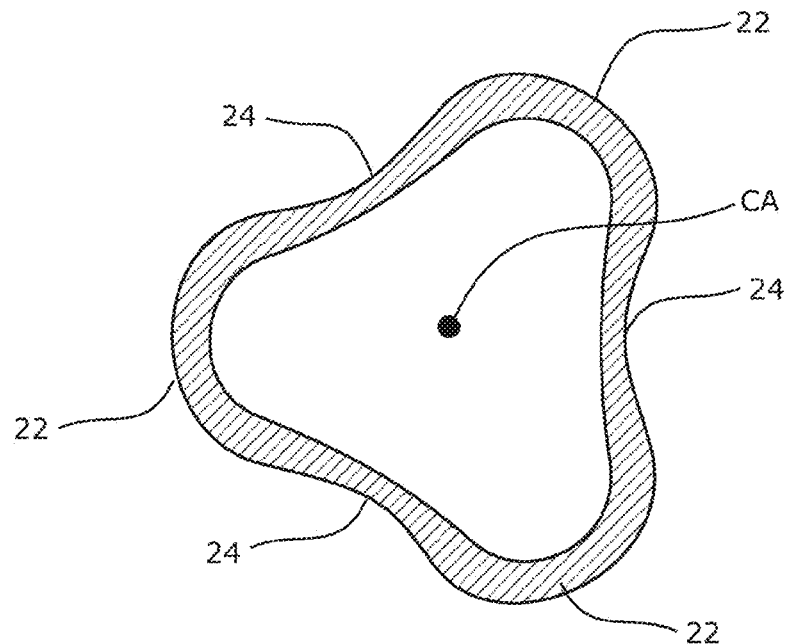
FIGS. 10-13 are sections of different bias flow valve configurations having differing numbers of lobes and/or differing lobe constructions.
Figure 11:
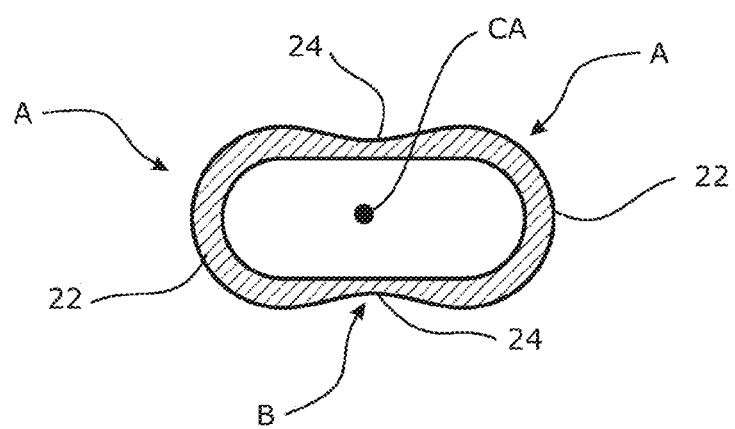
Figure 12:
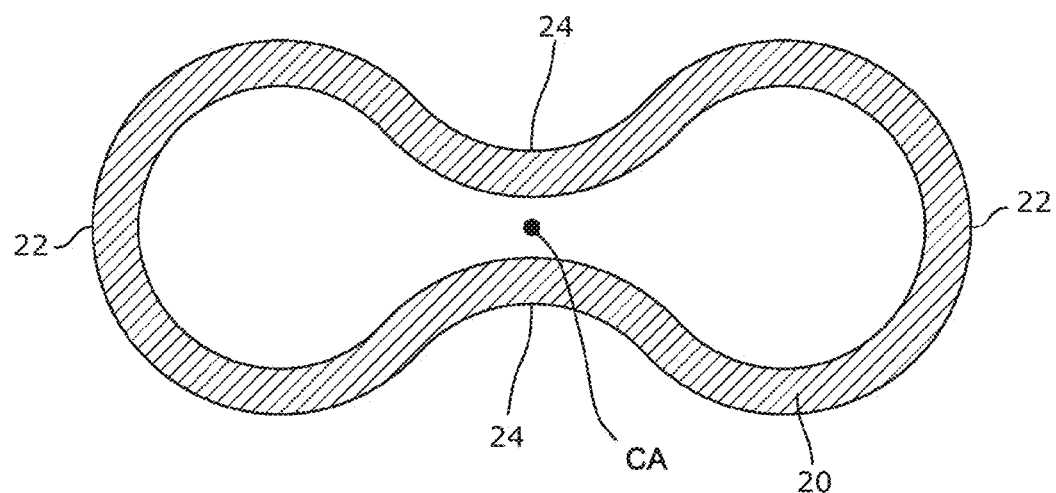
Figure 13:
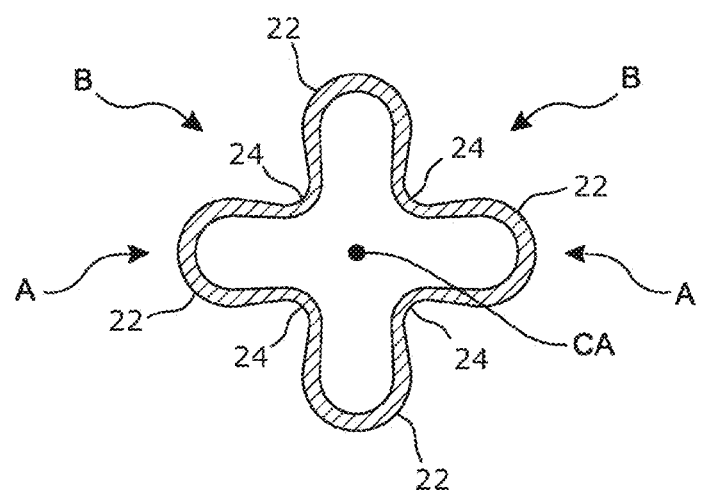

Any number of lobes can be used. More than one lobe has been found to be easier to design and manufacture that a single lobe in order to get the desired repeatability and controllable closing of the opening. FIG. 10 shows a three lobe configuration. Each of FIGS. 11 and 12 shows a two lobe configuration. FIG. 13 shows a four lobe configuration. From a stability standpoint and an ease of design and manufacture standpoint, the three lobe configuration has been a favored configuration.

In some configurations, the lobes 22 can be symmetrically disposed about the central axis CA. In some configurations, the apex of each lobe 22 can be equidistant from the central axis CA. In other words, the apex of each lobe 22 is spaced from the central axis CA the same distance at the apex of each of the other lobes 22. In some configurations, the apex of each lobe 22 can be equidistant from the central axis CA with respect to the apex of any diametrically opposed lobe 22. In some configurations, the apex of each lobe 22 is equidistant from the central axis CA and an included angle between each of the lobes is equal for all of the lobes 22. In other words, the lobes 22 are symmetrically spaced about the central axis CA. In some configurations, the lobes 22 are not all symmetrically spaced about the central axis CA but are spaced in one or more symmetrical patterns. Other configurations also are possible.

In some configurations, an inner member 26 can be positioned within the valve 10. The inner member 26 can be used with any valve configuration described herein. The inner member 26 can be positioned in the region of the inlet 18. The inner member 26 can be a rigid tube in some configurations. The inner member 26 provides a minimum flow passage such that, if the membrane 14 were to collapse fully around the inner member 26, the inner member would maintain a flow path. As such, in some configurations, the inner member 26 is a single tube with an inner lumen 28. In some configurations, the inner member 26 is a plurality of posts that maintain a flow path through the valve 10 by reducing or eliminating the likelihood of a total closure of the valve 10. In effect, the inner member 26 can be any component that acts as a splint to hold open at least a portion of the valve 10 when the valve is in an otherwise closed position. The opening that is preserved can be related to a desired flow at the maximum operating pressure of the CPAP machine or other flow generator.

Figure 14:
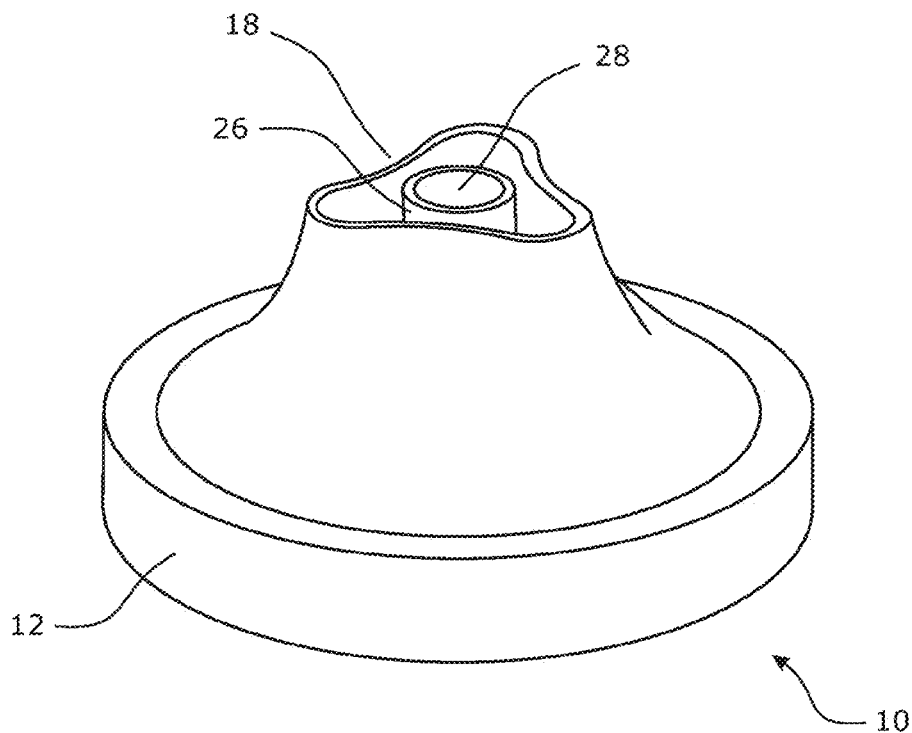
FIGS. 14 and 15 are bias flow valves arranged and configured in accordance with certain features, aspects and advantages of the present invention.
Figure 15:
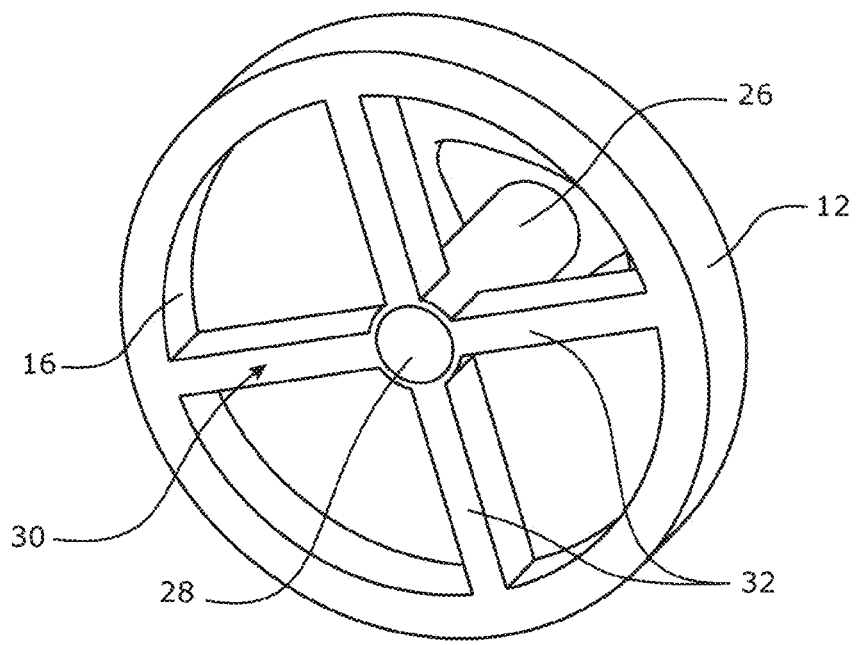

With reference to FIGS. 14 and 15, the illustrated inner member 26 is mounted to a support structure 30. The support structure 30 can support the inner member 26 in position without significantly impacting flow through the valve 10. The illustrated support structure 30 comprises one or more cross members 32. In the illustrated configuration, the inner member 26 can extend from the inlet 18 to the outlet 16 and can be supported at any desired location along the length of the inner member 26. In some configurations, the support structure 30 can be positioned within the base 12. In some configurations, the support structure 30 can be positioned adjacent to the outlet 16.

One or more of the adjacent regions of the valve can close off against an outer surface of the inner member 26 as the flow generator increases the pressure. Through the use of the inner member 26, a flow path through the valve 10 can be maintained. Such configurations can reduce or eliminate the likelihood of the valve 10 inverting, closing off completely at high pressures or overly limiting flow at higher pressures, which may occur, for example, when a user coughs. In some configurations, the inner member 26 can be formed of the same material as the rest of the valve 10. In some configurations, the inner member 26 can be formed of different materials relative to the rest of the valve 10. In some configurations, the inner member 26 can have a wall thickness of the same material as used for the membrane but with a wall thickness sufficient to maintain an open flow path through the membrane. In some configurations, the inner member 26 can be formed of the same material used to form the base 12.

In configurations now featuring the inner member 26, the shape and/or the varying thicknesses and/or stiffnesses surrounding the opening defined by the inlet 18 can help reduce or eliminate the likelihood of the valve 10 entirely collapsing and can help reduce or eliminate the likelihood of the valve 10 sticking shut in use. In constructions without the inner member 26 as well as those with the inner member 26, the wall thickness can change around a given cross section (see FIG. 6); the wall thickness also can change along the principal axis of the valve 10 (see FIG. 5). The illustrated changes in wall thickness help to provide a smooth constricting mechanism across the operating pressure range for treating sleep apnoea or other respiratory care patents.

Figure 6:
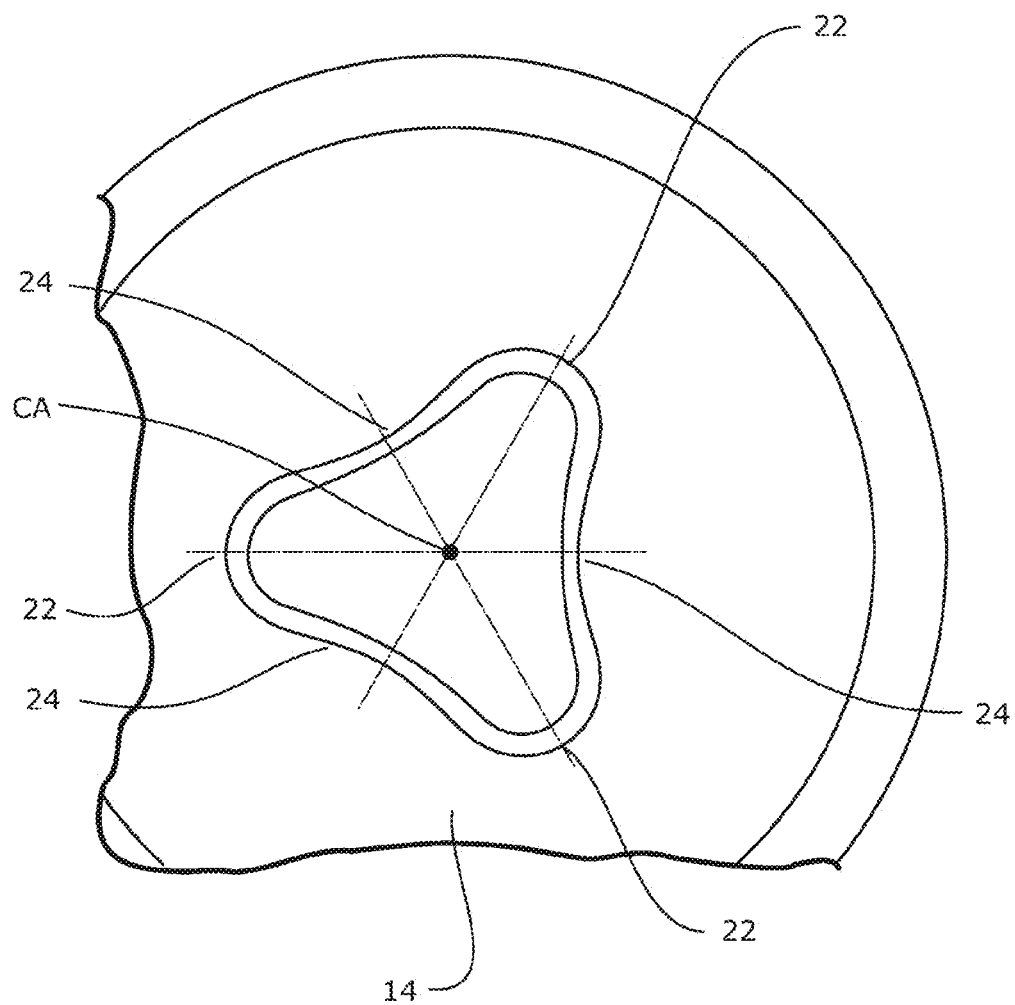
FIG. 6 is an enlarged view of a portion of the bias flow valve of FIG. 3.
Figure 8:
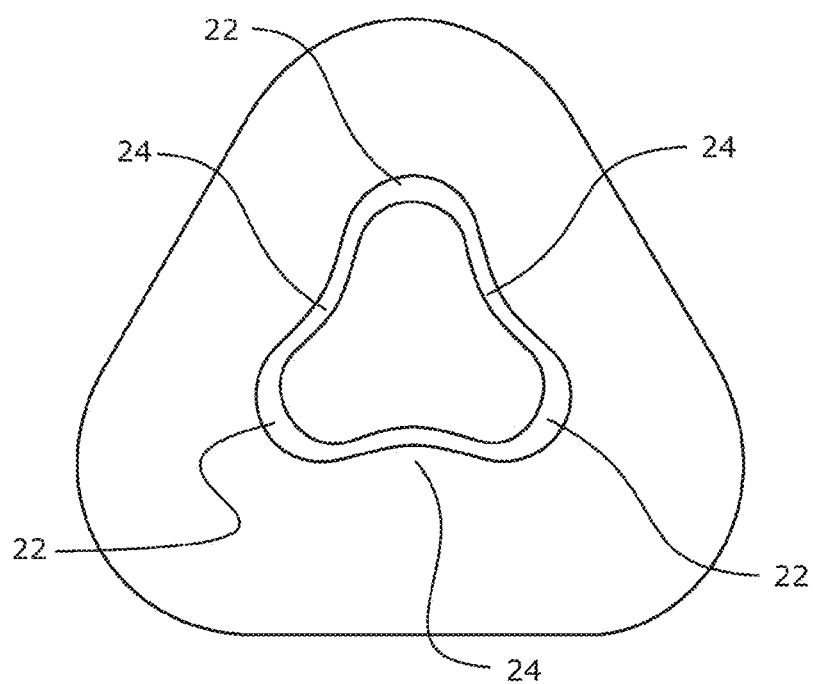
FIG. 8 is a top view of the bias flow valve of FIG. 7.

With reference again to FIG. 6, in some configurations, the wall thickness of the membrane can be varied at and/or near the rim 20. In some configurations, the wall thickness of the membrane can be varied at the rim 20 and axially along at least a portion of the membrane in the direction of the outlet outer rim 20. Such a wall thickness variance is shown in the cross section of FIG. 5, where the wall tapers from the base 12 to the inlet 18. As also illustrated in FIG. 6 and FIG. 8, for example, the wall defined by the membrane 14 can be relatively thicker in the lobes 22 and relatively thinner in the bridging portions 24. Such a configuration increases the likelihood of controlled collapsing of the inlet 18 when pressure is applied to the outer wall of the membrane 14.

If the thickness in the bridging portions 24 is too thick, then the valve 10 may be less deformable and may not close enough and, if the thickness in the bridging portions 24 is too thin, then the valve 10 may be too deformable and may close too much. In some silicone rubber configurations, the wall sections of the constructed valve 10 can be in the range of 100 to 400 microns for the relatively thicker portions and 50 to 300 microns for the relatively thinner portions. In the configuration of FIG. 6, the apexes of the lobes 22 can have a thickness of 300 microns while the middle region of the bridging portions 24 can have a thickness of 200 microns. A transition between the thicker lobes 22 and the thinner portion of the bridging portion 24 (that is, a transition between the concave lobes 22 and the convex bridging portions 24) can assist in resisting collapse of the valve 10. If the outer radius of the lobes 22 is reduced from 1.3 mm to 1.2 mm or 1.25 mm, the valve 10 of FIG. 6 collapses too easily. The centres of the inner and outer radii of the concave portions 22 in the valve 10 of FIG. 6 are offset by 0.1 mm along radial axes that extend from the centre of the opening.

As illustrated in, for example, FIG. 12, the wall of the membrane 14 that defines the lobes 22 and the bridging portion 24 can have a uniform thickness about the entire periphery of the rim 20. In some such configurations, the geometry can be tuned to obtain the desired collapsing characteristics. In some such configurations, the material can be varied to provide a stiffer portion in the lobes 22 and a more flexible portion in the bridging portions 24. Any other suitable combination of these or any other suitable configuration can be used to obtain a valve that at least partially collapses upon itself as described herein.

Figure 9:
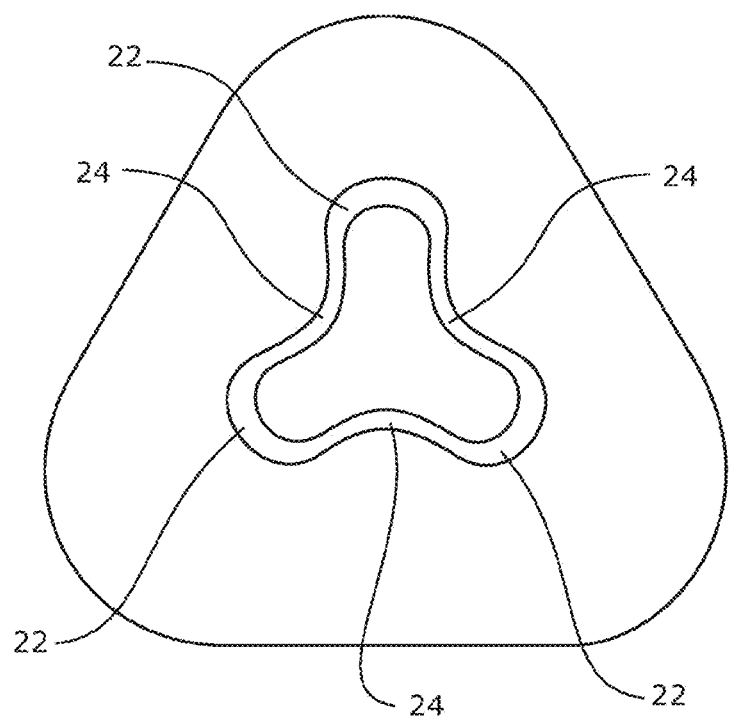
FIG. 9 is a top view of the bias flow valve of FIG. 7 when subjected to higher pressures.

The lobes 22 provide stiffness to reduce or eliminate the likelihood of the valve inverting under high pressures. In general, however, the stiffness of the membrane 14 is defined by the thickness in the lobes 22, the profile of the wall, the height of the valve 10 and the properties of the material used to make the valve. As shown in FIGS. 8 and 9, the valve 10 deforms in a way that narrows the flow passage and, thereby, reduces the level of flow that can be passed through the valve 10. In FIG. 8, the valve is shown with no operating pressure (that is, 0 cmH2O) while, in FIG. 9, for example, the valve is shown under a pressure of greater than 1 cmH2O. As shown in FIG. 9, under the application of pressure to the membrane 14, the thinned wall section deforms, which results in changes to the flow passage defined through the lobe 22 cross sectional area changing, which in turn changes the flow rate that is possible through the flow passage defined through the lobe 22 based on the pressure differential that exists across the valve 10. By varying the relative portions of the thick to thin (or more stiff to more flexible), the performance of the valve 10 can be tuned for specific operating pressure ranges. In some configurations, one or more deformable orifice does not entirely collapse within the range of normal operating pressures. In some configurations, each lobe can include one or more surface and the one or more surfaces do not come into contact with itself or themselves within the range of normal operating pressures. Thus, one or more of the lobes, the bridging portions and the varied thicknesses, at least in part, can define means to regulate a flow of gas based on the applied pressure.

Valve Arrays

Figure 16:
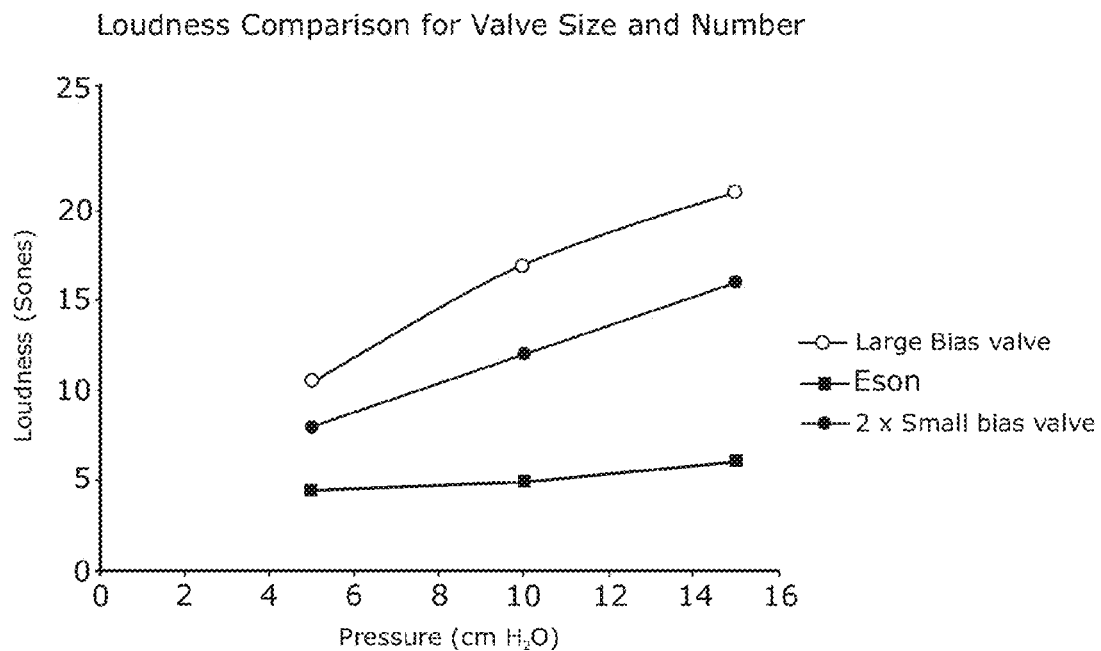
FIG. 16 is a graphical depiction of the effect of valve size and valve number on pressure and loudness.
Figure 42:
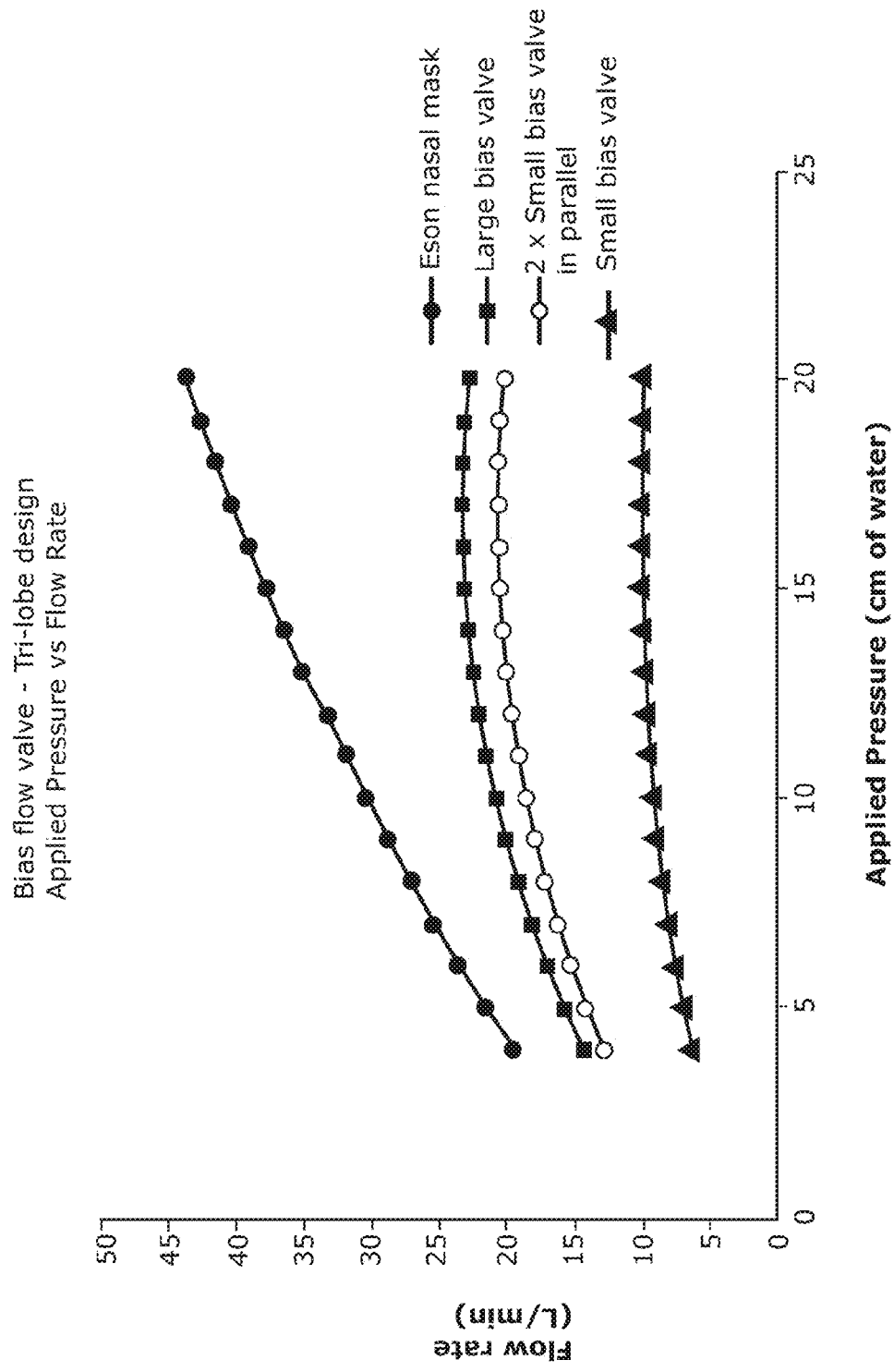
FIG. 42 is a graphical depiction of the impact of parallel bias valves on flow rate.

As shown in FIG. 42, using multiple small valves 10 can approximate the flow characteristics of a single larger valve, but using multiple small valves 10 can reduce the noise relative to using a single valve 10 having the same throughput. This is because the multiple small flow restrictions will result in small pressure drops across each valve resulting in less turbulence and less noise generation. This is demonstrated in the graphical depiction of FIG. 16. As illustrated, within increasing pressures, a single large valve arranged and configured in accordance with certain features, aspects and advantages of the present invention is demonstratively louder than two small valves. Moreover, the data shows that the increase in loudness for two smaller valves increases significantly less over the illustrated larger valve.

With reference now to FIGS. 17-24, any configuration of the valve 10 described above can be used in a valve array 40. The valves 10 used in an array can be miniaturized relative to a single valve 10. To be clear, the valves 10 that make up the valve array 40 can be uniform in configuration or can be assorted in configuration. In some valve arrays 40, the valves 10 are configured to have the same operating characteristics uniformly across the field of the array 40. In some valve arrays 40, one or more of the valves 10 may be configured to behave differently relative to others at the same operating pressures. In some configurations, twenty valves will be used to provide an approximate cross sectional area of about 22 mm2. Other numbers of valves can be used and other cross sectional areas can be used.

Figure 17:
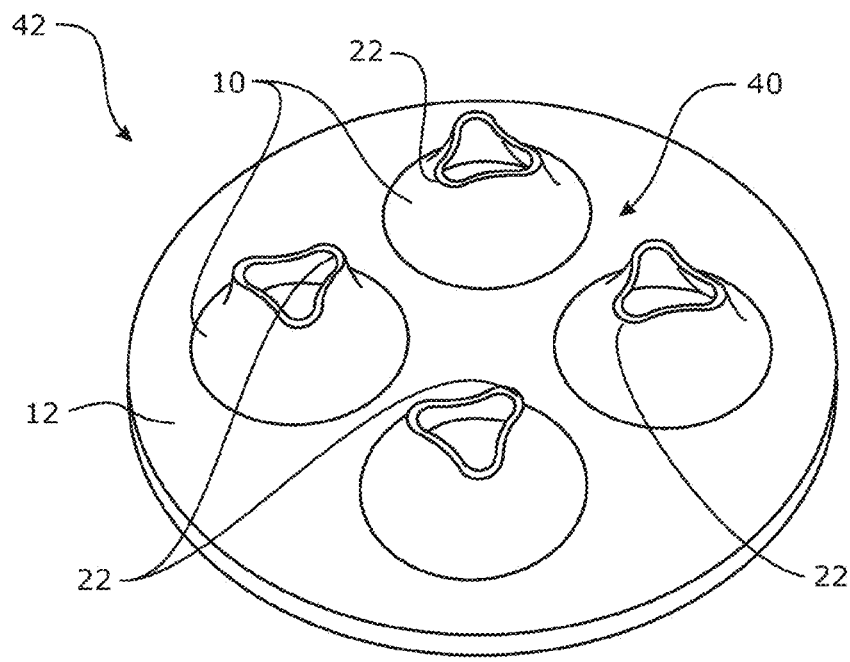
FIGS. 17-24 are various configurations featuring a plurality of bias flow valves in valve arrays.

With reference to FIG. 17, a multivalve component 42 is illustrated. The multivalve component 42 comprises an array 40 of valves 10. The valves 10 are configured as described above. A common base 12 connects the valves 10 in the illustrated configuration. In some configurations, the common base 12 can be formed in multiple pieces that are connected or interconnected. In some configurations, the base 12 of each valve can be received within a receptacle or opening of a plate that serves as the common base. Any other configurations can be used.

With continued reference to FIG. 17, the valves 10 in the illustrated configuration are spaced in a symmetrical pattern. The rotational orientation of the valves 10 is such that two of the valves 10 are rotated 180 degrees relative to two of the other valves 10. In other words, the apex of the lobes 22 of two of the valves 10 points toward the apex of the lobes 22 of the other two of the valves 10. In some configurations, the four valves 10 can be orientated such that one of the lobes 22 of each of the valves 10 points toward a center of the multivalve component. Other orientations of the valves 10 also are possible.

Figure 18:
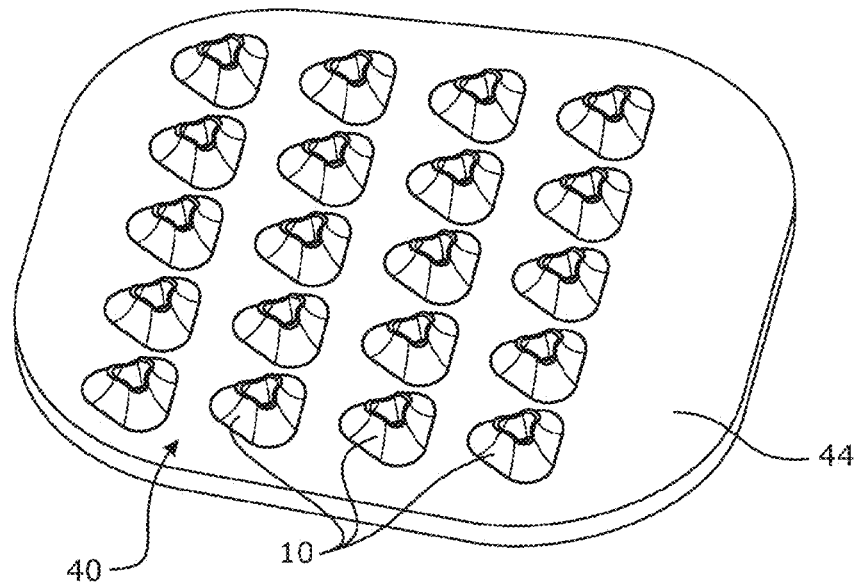

With reference now to FIG. 18, the illustrated array 40 of valves 10 is shown on a multivalve insert 44. The multivalve insert 44 can comprise any desired number of valves 10 to provide a desired level of flow. In the illustrated configuration, the multivalve insert 44 comprises twenty valves 10. The valves are arranged in four rows and five columns in the illustrated configuration. In the illustrated configuration, the valves 10 also are oriented in a single direction. Other configurations are possible.

The multivalve insert 44 can be formed in any suitable manner of any suitable material. For example, in some configurations, the multivalve insert 44 can be formed of a single material. In some such configurations, the entire multivalve insert 44 can be formed of a material such as silicone or any suitable thermoplastic elastomer. The configuration of FIG. 18 is completely formed of a single such material.

Figure 19:
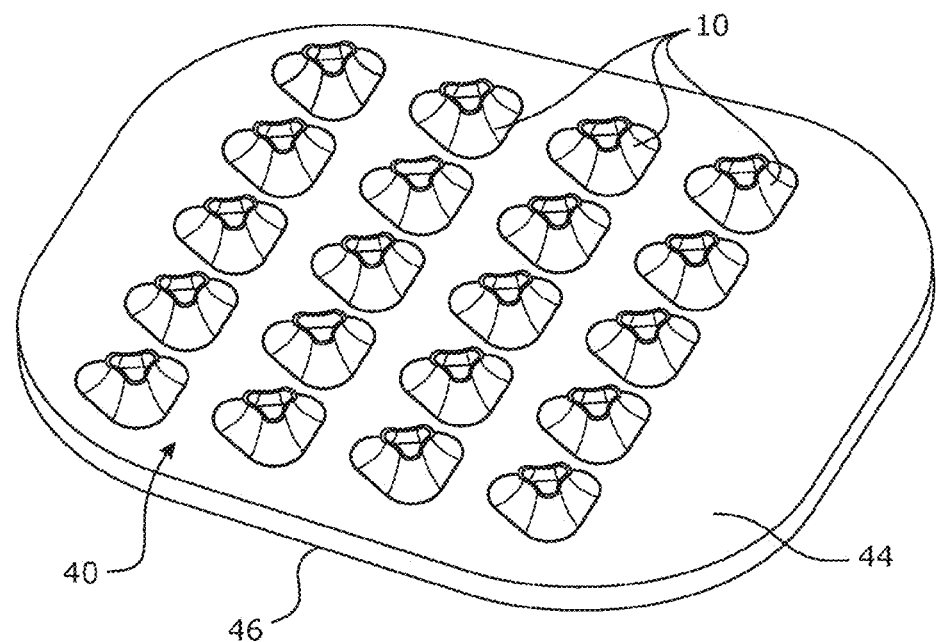

With reference to FIG. 19, the illustrated multivalve insert 44 is the same as the multivalve insert 44 illustrated in FIG. 18 except the multivalve insert 44 in FIG. 19 comprises a substrate material 46. The substrate material 46 can be the same material used to form the valves 10 or can be a different material. In some configurations, the substrate material 46 provides a rigid base for the valves 10 of the multivalve insert 44.

Figure 20:
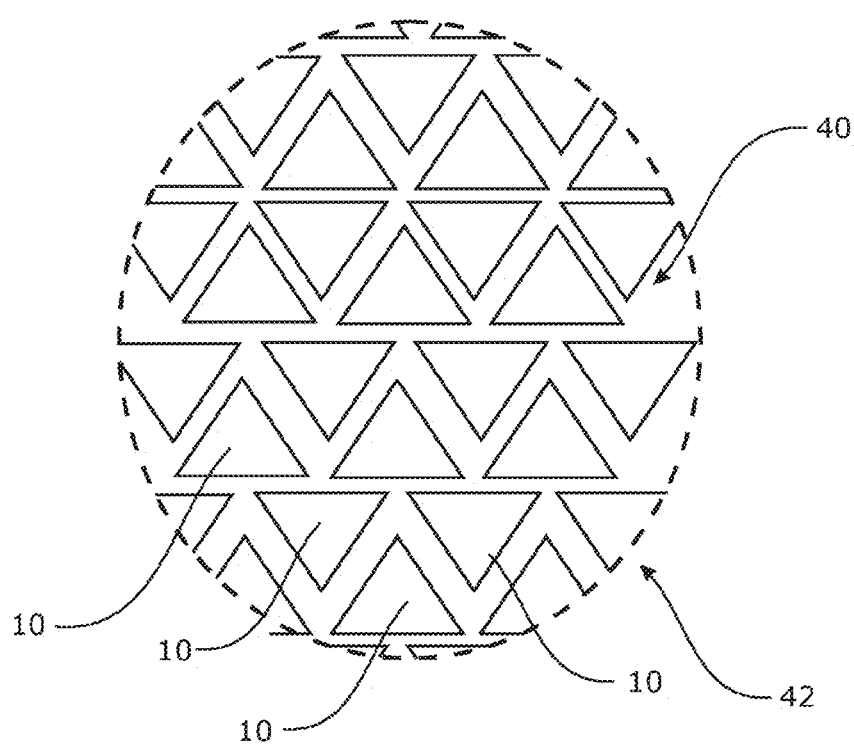

FIG. 20 schematically illustrates another multivalve component 42. The multivalve component 42 illustrated in FIG. 20 comprises a plurality of rows of valves 10. The valves 10 have one row with a first orientation and a second row with an opposite orientation; the two adjacent rows of valves 10 are nested. By nesting the valves 10, a greater valve density can be obtained.

Figure 21:
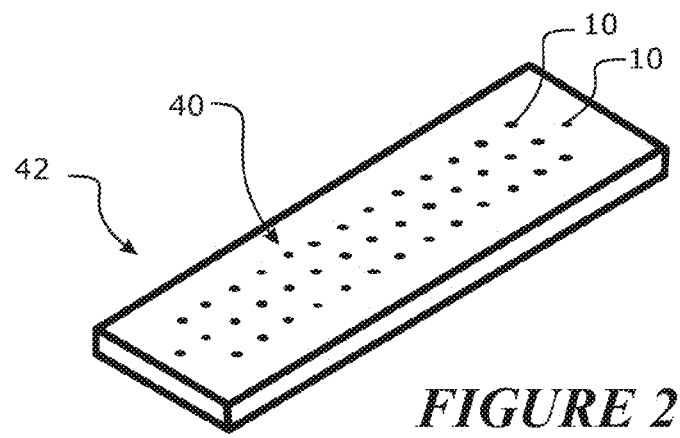

With reference now to FIG. 21, a further valve array 40 on a multivalve component 42 is illustrated. The valves 10 in the illustrated configuration are arranged in a pattern of rows having unequal numbers of valves 10. The illustrated configuration features three rows of valves 10 with the center row having more valves 10 than the outer rows. In particular, the center row has one additional valve 10 at each end of the row.

Figure 22:
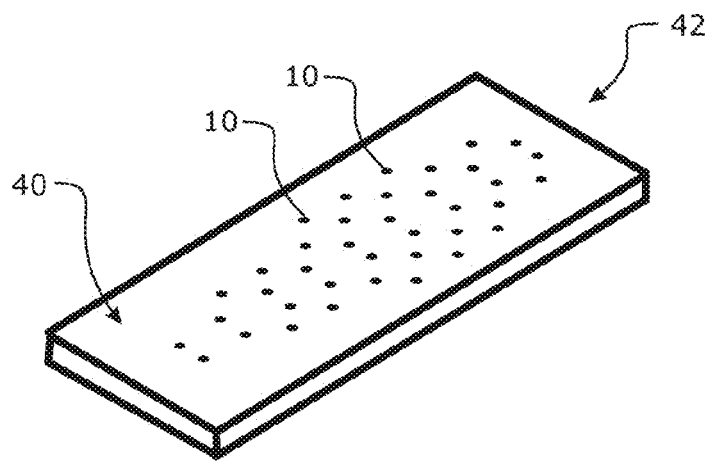

FIG. 22 illustrates a valve array 40 on a multivalve component 42. The valves 10 in the valve array 40 have a non-linear layout. The valves 10 may be arranged in a manner that can be predetermined by the designer.

Figure 23:
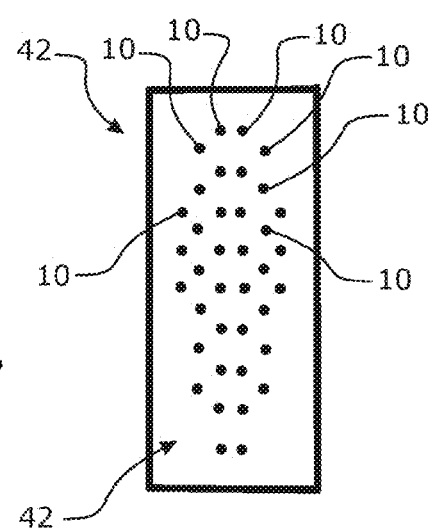

FIG. 23 illustrates another valve array 40 on a multivalve component 42. In the illustrated configuration, the valves 10 are arranged in different rows. The center two rows have nine valves 10 arranged side-by-side. Each of the center rows is flanked by an intermediate row that is in turn flanked by an outside row. Each intermediate row includes seven valves 10. Each outside row includes three valves 10. The valves 10 in the outside rows can be aligned with the valves 10 in the center rows while the valves 10 in the intermediate rows can be offset from the valves in the center rows and the outside rows.

Figure 24:
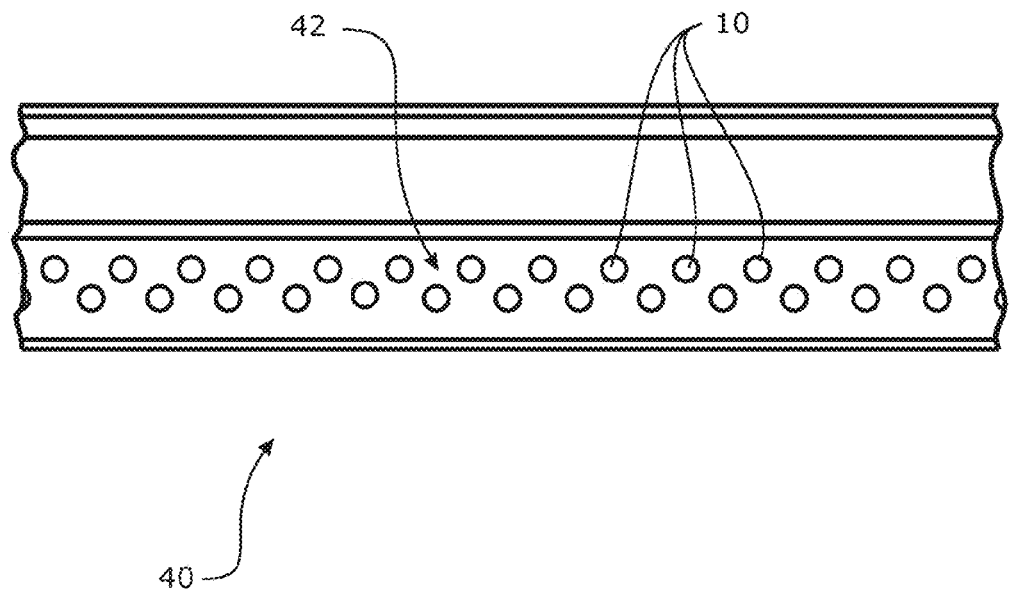

FIG. 24 shows a further valve array 40 on a multivalve component 42. In the illustrated configuration, the valves 10 form two staggered lines. The valves 10 can be used to like the periphery of a component of a mask system or the like.

Any of the valve configurations described herein can be incorporated into a breathing mask or related component. For example, the valve arrays 40 can be incorporated into a nasal mask, a pillows mask, a full face mask, a conduit, an elbow, or the like. In addition, it is possible to integrate traditional bias flow holes into the valve arrays such that the bias flow holes and the valves 10 are used together in a single array or component. In some configurations, a line of valves can be flanked by a row of bias flow holes. In some configurations, a line can contain valves and bias flow holes. Any other suitable configuration can be used.

System Components Featuring Valves

In the following discussion, the term "valve" will include "valve array" unless otherwise apparent. The bias flow control valve 10 can be positioned in any suitable location keeping in mind a desire to allow evacuation of carbon dioxide from within the system where the carbon dioxide is introduced through exhalation. The valve 10 preferably is not the only flow path between the patient and the flow generator (for example, CPAP). In other words, the air flow must have a path to travel from the flow generator to the patient without passing through the valve 10. Without the alternative flow path, the pressure drop through the valve 10 would mean that the patient was not receiving the prescribed pressure. The valve 10 can be placed anywhere in the system that a bias vent arrangement could be placed. In some configurations, the valve 10 can be placed in front of or behind or as a replacement for the bias vent arrangement. Further, the valve 10 can be placed so that the axis of the valve 10 is perpendicular to the surface or can be on an angle to the surface in order to better provide directional control to the flow emanating from the valve 10.

In some configurations, the valve 10 can be positioned between the patient and the bias flow holes. In some configurations, however, such a positioning may lead to increased noise and/or decreased or impaired valve performance. For example, a system with a larger pressure drop across the bias flow holes (for example, a smaller cross sectional area of the holes) than across the valve 10 could decrease the performance of the valve 10. To address such an issue, the valve 10 could be provided with less stiffness. In some configurations, a system with a pressure drop that is higher across the valve than the bias flow holes could result in increased noise generation as the air jets exit the surface and through the bias flow holes. This can be reduced by having a larger chamber between the bias flow holes and the valve and by minimizing the pressure drops between the two parts. In some configuration, this can be addressed by providing a hollow frame or shroud through which venting can occur.

Figure 25:
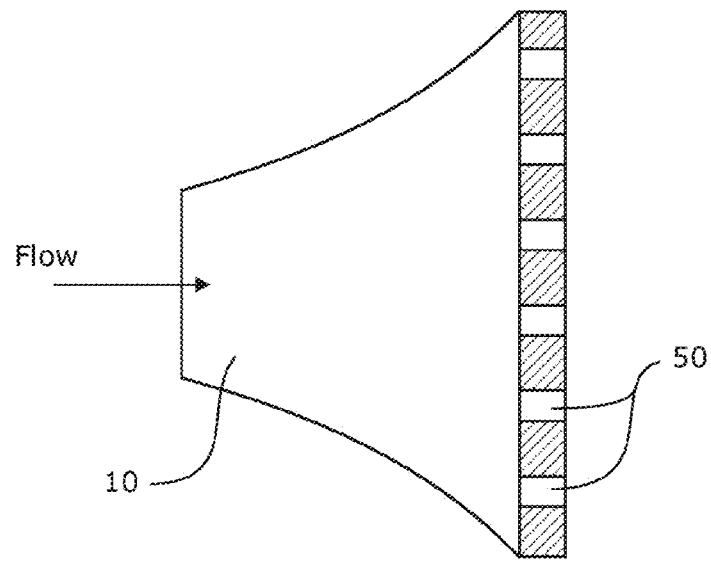
FIG. 25 is a bias flow valve in combination with a bias material.

With reference to FIG. 25, the valve 10 can be placed in line with one or more bias flow holes 50. By positioning the valve 10 in line with the bias flow holes 50, the holes 50 can quiet the sound of a larger valve 10. This is particularly advantageous because a larger valve 10 is easier to manufacture than the smaller valves used in the valve arrays 40 discussed above. It is possible to place a valve array 40 in line with the bias flow holes 50 as well. It also is possible to use a diffuser in place of or further in line with the bias flow holes 50.

In some configurations, the bias flow control valve 10 can be positioned on an interface. In some configurations, the bias flow control valve 10 can be positioned on a mask. In some configurations, the bias flow control valve 10 can be positioned on a connector that is positioned between a conduit and a mask. In some configurations, the bias flow control valve 10 can be positioned on a conduit that connects to the mask. The bias flow control valve 10 can be used with any suitable mask configuration (not shown). The mask can include a body portion sized and shaped to surround the nose and/or mouth of the user. The mask can be adapted to create at least a substantial seal with the user's face. The body portion of the mask can have an interior and an exterior. The mask can include a coupling that permits the patient interface to be coupled to the gas delivery system. The bias flow control valve 10 allows the passage of gas from the interior of the body portion of the mask to the exterior of the body portion of a mask.

Figure 26:
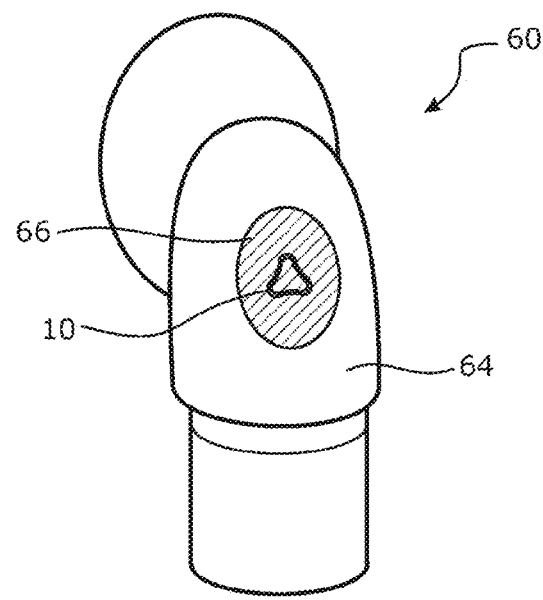
FIGS. 26 and 27 illustrated a bias flow valve in combination with an elbow.
Figure 27:
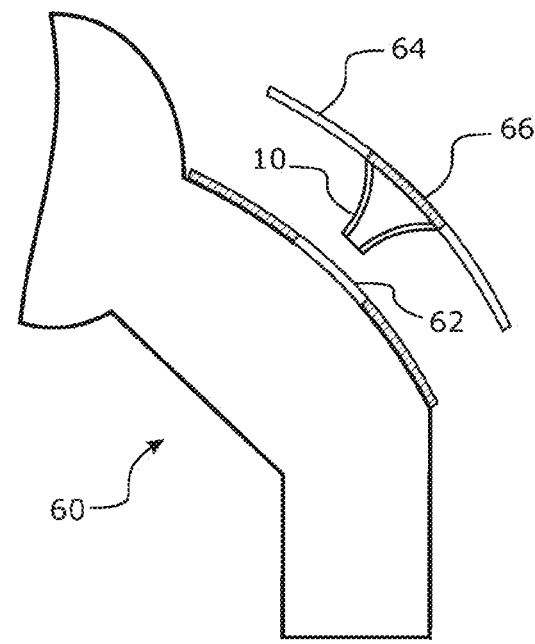

With reference now to FIGS. 26 and 27, the valve 10 can be mounted to a connector structure, such as an elbow 60. As illustrated, the elbow 60 can include an opening 62. The opening can receive at least a portion of the valve 10. In some configurations, the valve 10 is mounted to a cover 64. The cover 64 can be permanently secured or removably connected to the elbow 60. In some configurations, the valve 10 and the cover 64 can be connected by overmoulding or the like. In some configurations, a bias material 66 can be mounted to the cover 64 or otherwise be positioned such that flow through the valve 10 also flows through the bias material 66. The bias material can be a group of bias flow holes or a diffuser scrim material or the like. While the illustrated configuration is on an elbow, a similar configuration can be used elsewhere on the mask, on the conduit or on a connector, for example.

Figure 28:
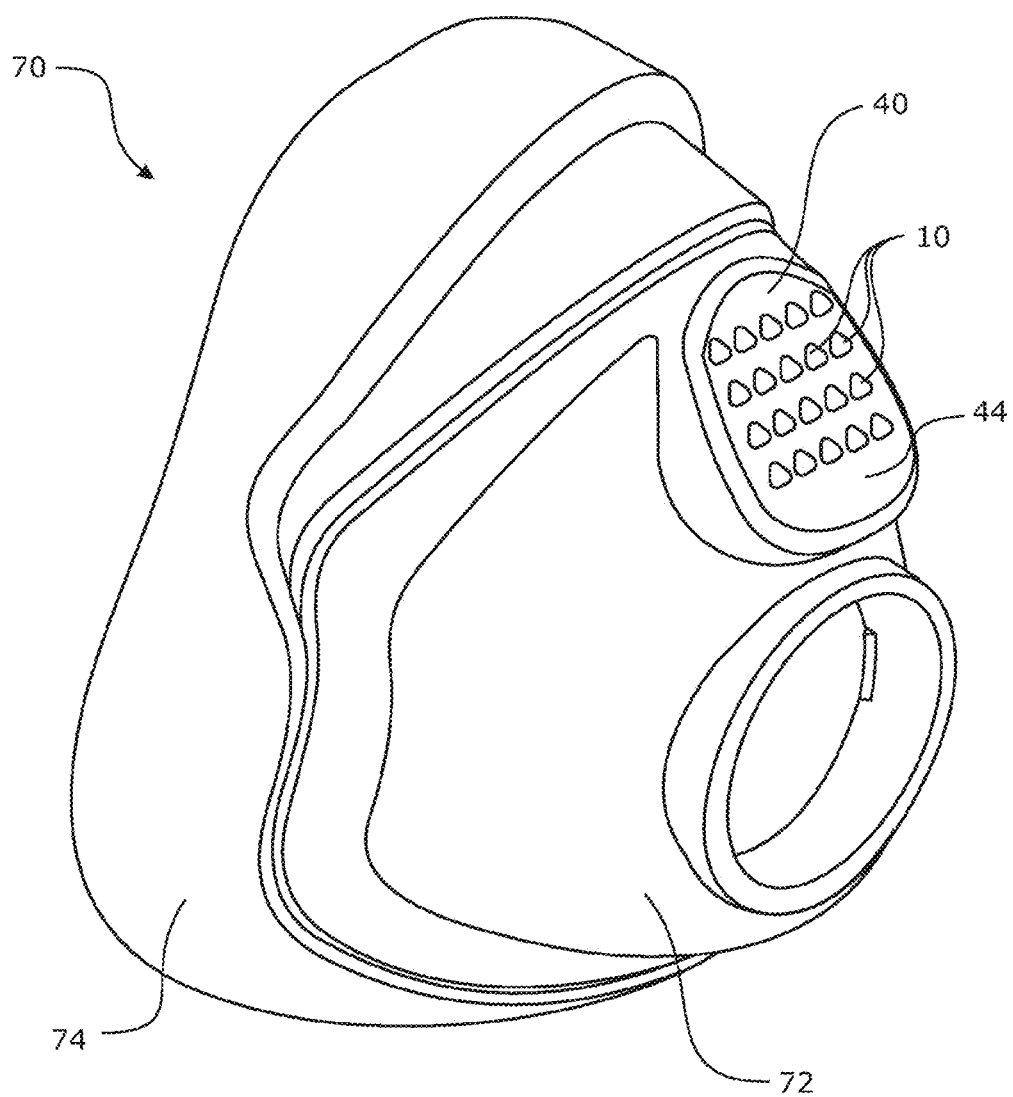
FIGS. 28-30 illustrate a mask in combination with a valve array.
Figure 29:
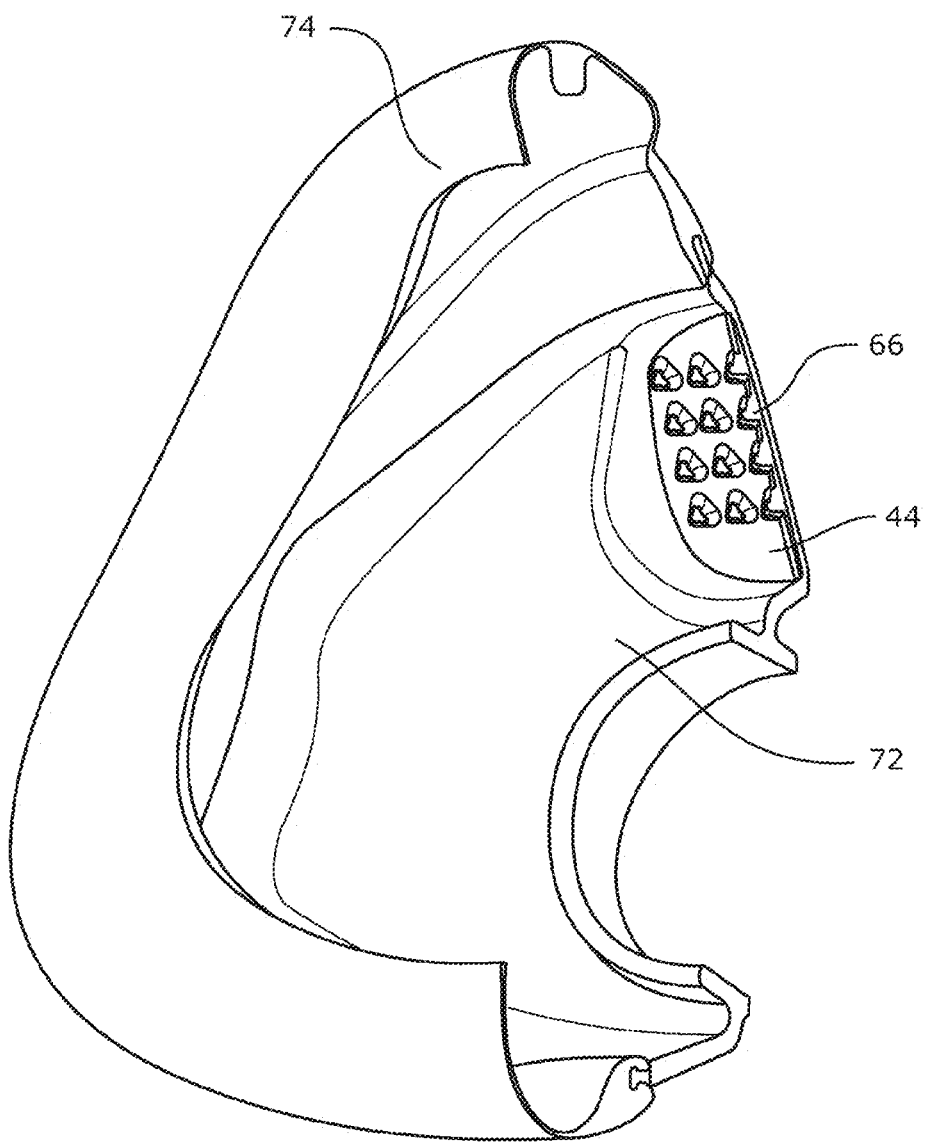
Figure 30:
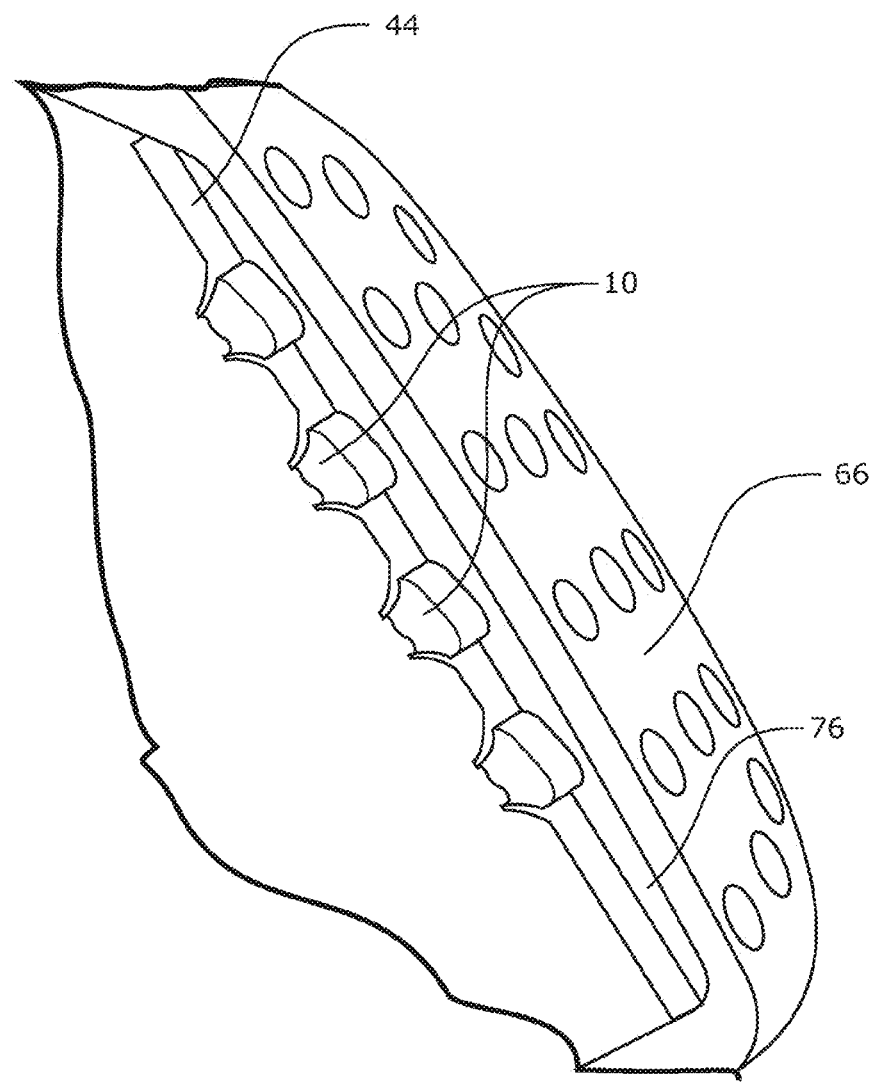

With reference now to FIGS. 28-30, a mask 70 is illustrated that integrates a valve array 40 that is arranged and configured as described above. The mask 70 generally comprises a seal housing 72 and a cushioning seal 74.

In the illustrated configuration, the seal housing 72 comprises a multivalve insert 44 such as that described above, for example but without limitation. The multivalve insert 44 can be removable in some configurations (for example, clipped into position). The multivalve insert 44 can be moulded into the mask 70 (for example, moulded into the seal housing 72). As described above, the valves 10 can be supported by a flexible base or can be supported by a more rigid substrate material. In some configurations, instead of the multivalve insert 44 featuring multiple valves 10, a single valve 10 can be used. In some configurations, instead of one valve array 40, more than one valve array 40 can be used (that is, more than one group of valves).

In the event that no biasing material is used such that the valve 10 or valves 10 vent directly to atmosphere, then multiple valves 10 are preferred. In the illustrated configuration, however, a plenum chamber 76 is defined between the multivalve insert 44 and a biasing material 66. The plenum chamber 76 can be larger than illustrated in some configuration. In addition, it is possible to include a hollow frame that the valve or valve array vents into.

Figure 31:
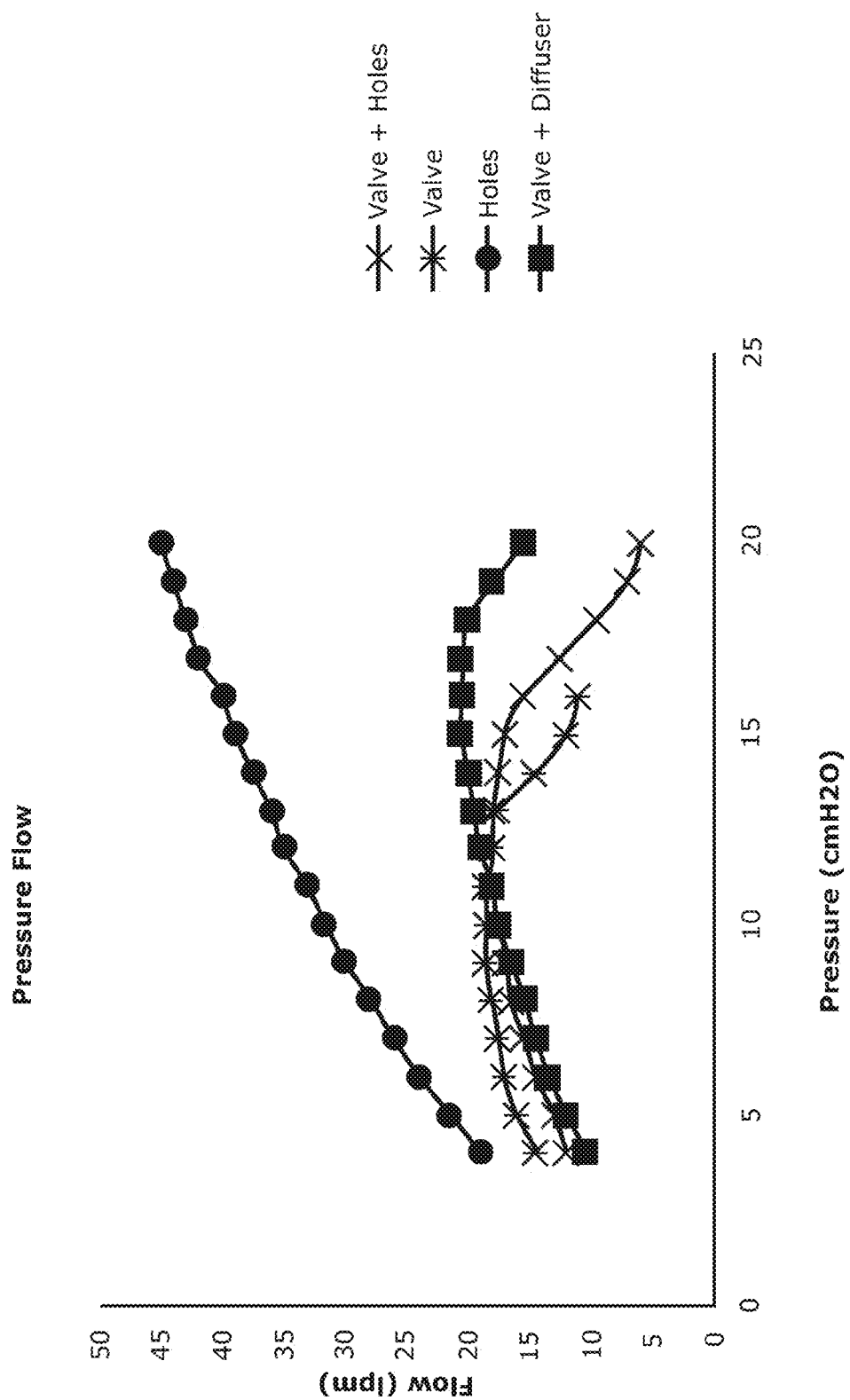
FIG. 31 is a graphical depiction of various combinations of valves, bias flow holes and diffusers and the impact of each combination on pressure and flow.
Figure 32:
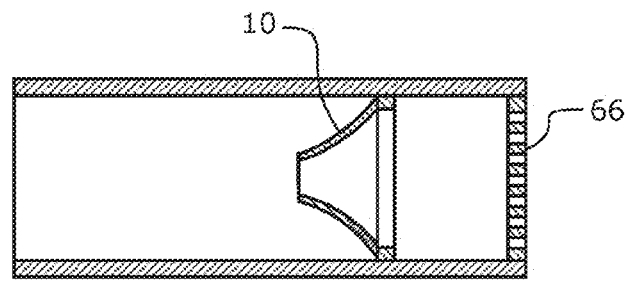
FIG. 32-35 show the combinations used to generate the graphical depiction of FIG. 31.
Figure 33:
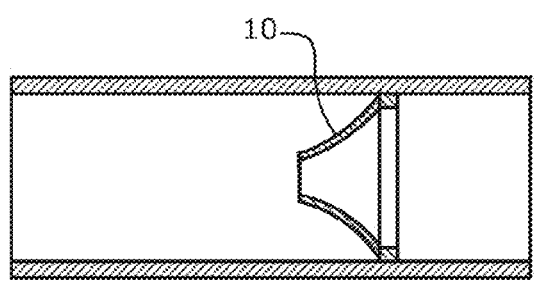
Figure 34:
Figure 35:
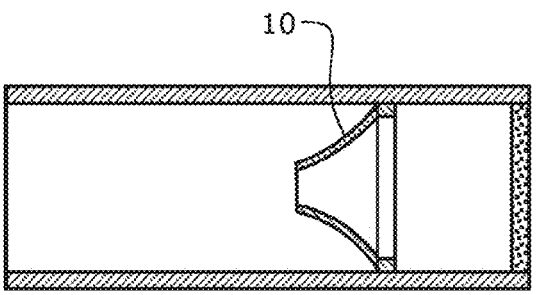

With reference to FIG. 31, a graphical depiction is provided that shows various flows at various pressures for embodiments of the mask 70 that include: (1) a large valve with bias flow holes; (2) a large valve; (3) bias flow holes; and (4) a large valve with a diffuser material. These configurations are illustrated in FIGS. 32-35. As illustrated in the graphical depiction, having the bias flow holes changes the performance of the mask 70. The maximum flow rate is approximately the same as when there are no holes in line with the valve, but the flow does not drop away until a higher pressure is applied. Having the bias flow holes in line with the valve would therefore be improved by changing the valve configuration, but does not necessarily result in a reduction of performance of the mask 70.

Figure 36:
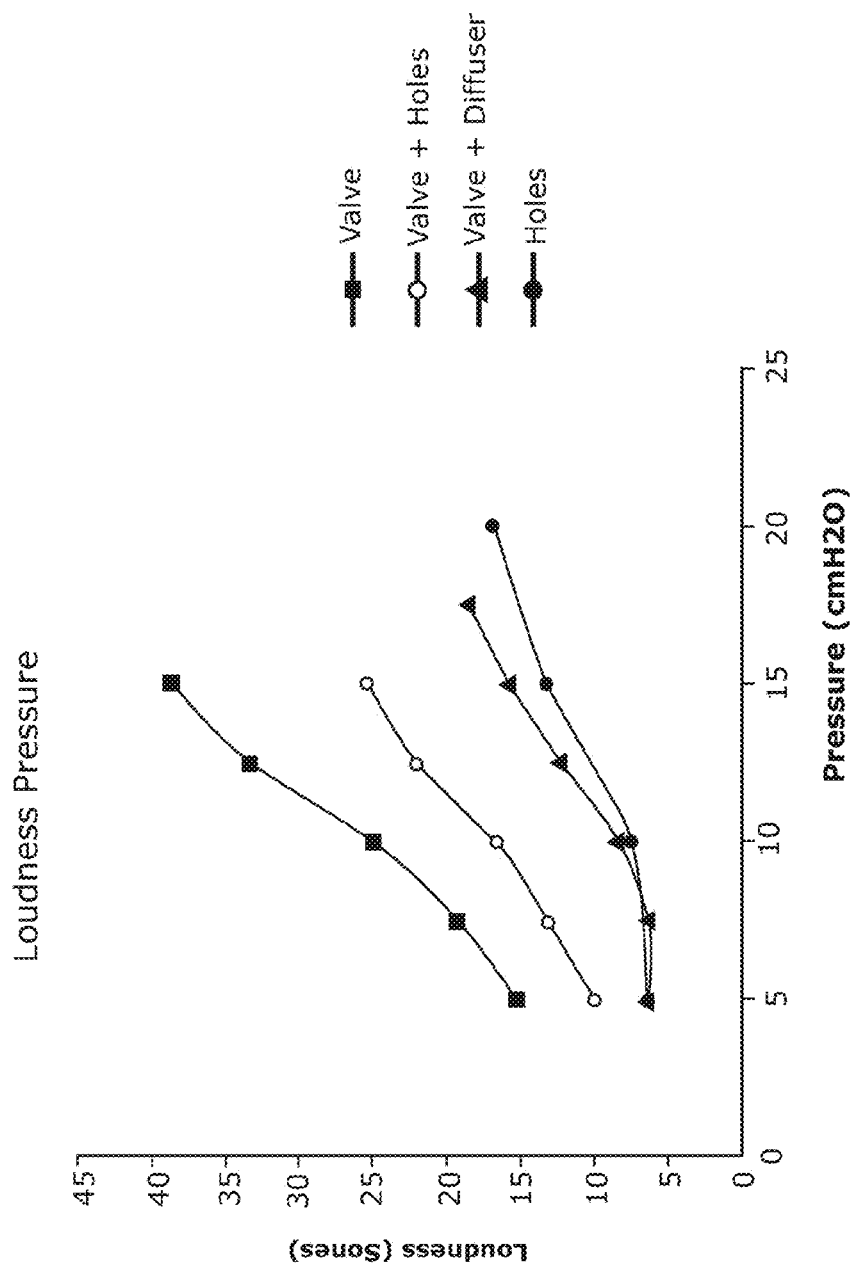
FIG. 36 is a graphical depiction of the effect of the combinations of FIG. 32-35 on pressure and loudness.

With reference to FIG. 36, a graphical depiction is provided that shows various loudness data points at various pressures for the same embodiments of the mask 70 as discussed directly above. As can be seen, in order to reduce the noise of the valve 10, it is best to incorporate a diffuser material after the valve.

Figure 37:
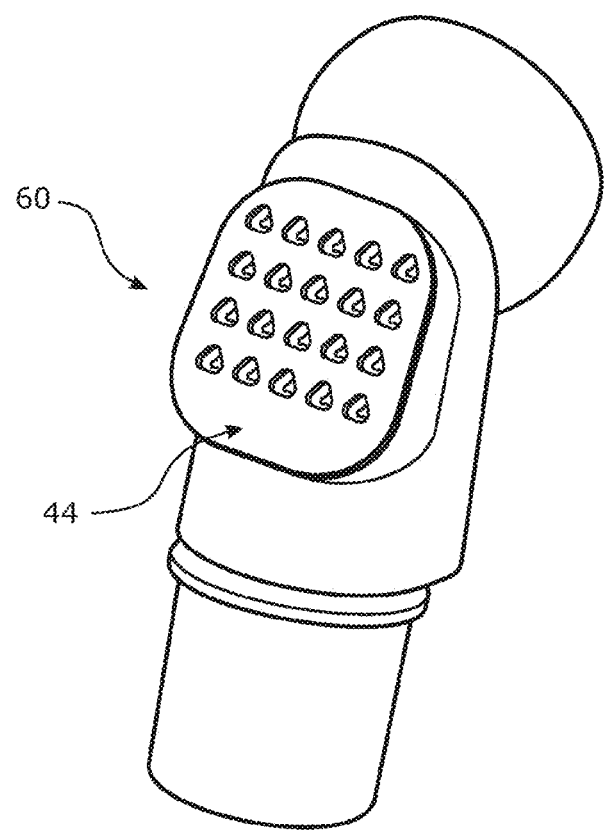
FIGS. 37-41 illustrate combinations of valves and other components in a CPAP system.

FIG. 37 illustrates another configuration in which the multivalve insert 44 is positioned on the elbow 60. The configuration can be similar to that shown in FIGS. 28-30 and can incorporate the same elements: the valves 10, the valve array 40, the multivalve insert 44, the bias material 66, and the plenum chamber 76. In the illustrated configuration, the elbow 60 comprises the multivalve insert 44, such as that described above, for example but without limitation. The multivalve insert 44 can be removable in some configurations (for example, clipped into position). The multivalve insert 44 can be moulded into the elbow 60. As described above, the valves 10 can be supported by a flexible base or can be supported by a more rigid substrate material. In some configurations, instead of the multivalve insert 44 featuring multiple valves 10, a single valve 10 can be used. In some configurations, instead of one valve array 40, more than one valve array 40 can be used (that is, more than one group of valves).

In the event that no biasing material is used, such that the valve 10 or valves 10 vent directly to atmosphere, then multiple valves 10 are preferred. In the illustrated configuration, however, a plenum chamber (not shown but similar to that of the mask embodiment) is defined between the multivalve insert 44 and a biasing material 66. It is possible to include a hollow frame that the valve or valve array vents into.

Figure 38:
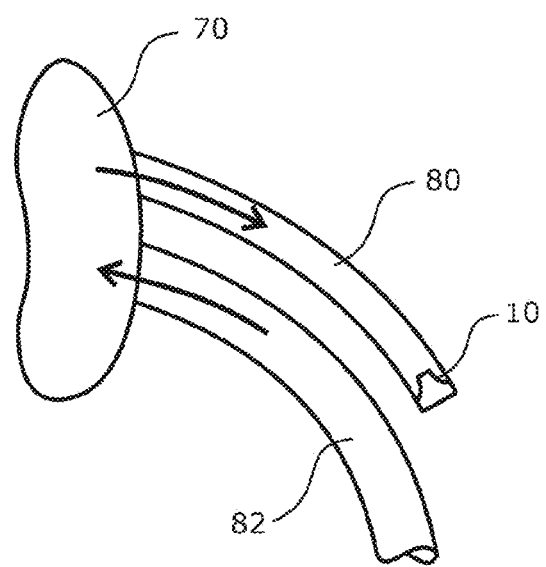

FIG. 38 illustrates a configuration in which a secondary exhaust tube 80 can be provided to the mask 70. The secondary exhaust tube 80 can include a valve 10 at the end of the exhaust tube 80. The valve 10 can restrict exhaust flow. The secondary exhaust tube 80 with the valve 10 provides a benefit of venting remotely from the user. In such remote locations, the noise of the valve is perceived to be less of a concern, for example. In some configurations, the secondary exhaust tube 80 can travel along at least a portion of a supply tube 82. In some configurations, the exhaust tube 80 can travel alongside of the intake tube 82. In some configuration, the exhaust tube 80 can be positioned coaxially within the intake tube 82. In some configurations, the exhaust tube 80 can surround at least a portion of the intake tube 82. Other configurations are possible.

Figure 39:
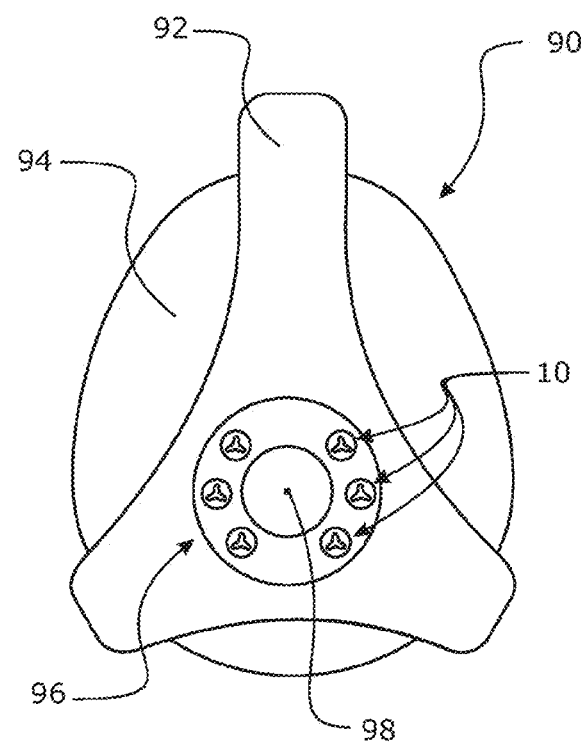

With reference to FIG. 39, a further configuration for a mask 90 is shown. The mask 90 includes a frame 92 to which a mask seal 94 can be secured. The mask frame 92 can include a ring 96. The ring 96 can at least partially encircle a socket 98 that receives an elbow, connector, conduit or the like. The ring can be provided with one or more valves 10. In some configurations, several small valves 10 can be disposed around the ring 96. By separating the valves, interference between the air flowing out of adjacent valves can be reduced, which thereby reduces turbulence and noise. In some configurations, the valves can be integrally formed with the ring 96 or other mounting structure. In some configurations, the ring 96 or other mounting structure can be integrally formed (for example, overmoulded) with the frame 92. In some configurations, the ring or other mounting structure can be removably attached to the frame 92. In some configurations, the ring or other mounting structure can be separately formed from the frame 92 and can be secured to the frame in any suitable manner.

Figure 40:
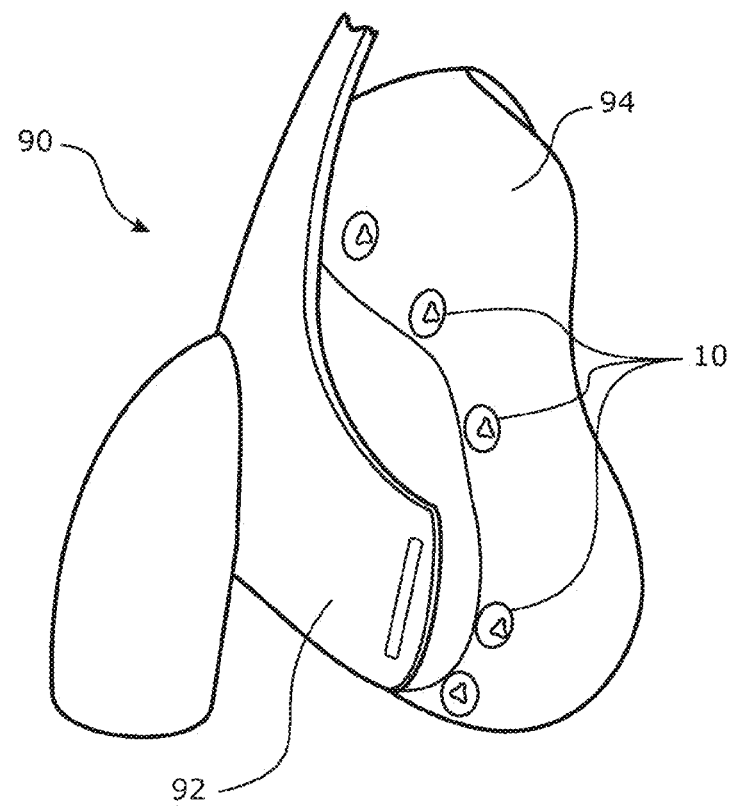

With reference to FIG. 40, a configuration of the mask 90 is shown in which the valves 10 are positioned on the mask seal 94. Because the mask seal 94 generally is formed of silicone or another similar material, the valves 10 can be integrated into the mask seal 94 and thereby reduce manufacturing steps. In some embodiments, the valves 10 can be grouped together on particular regions of the mask seal 94. In some configurations, there may be a group of valves 10 on each lateral side of the mask seal 94. In some configurations, there may be a group of valves 10 on the top of the mask seal 94. In some configurations, there may be a group of valves 10 on the bottom of the mask seal 94. Any combination of these groups also can be used. In some configurations, each of the valves 10 in any single group may be aligned in a single direction such that the flow from the valves 10 is in the same direction. In addition, aligning groups of valves advantageously simplifies manufacturing by providing a single draw plane for simplified moulding.

Figure 41:
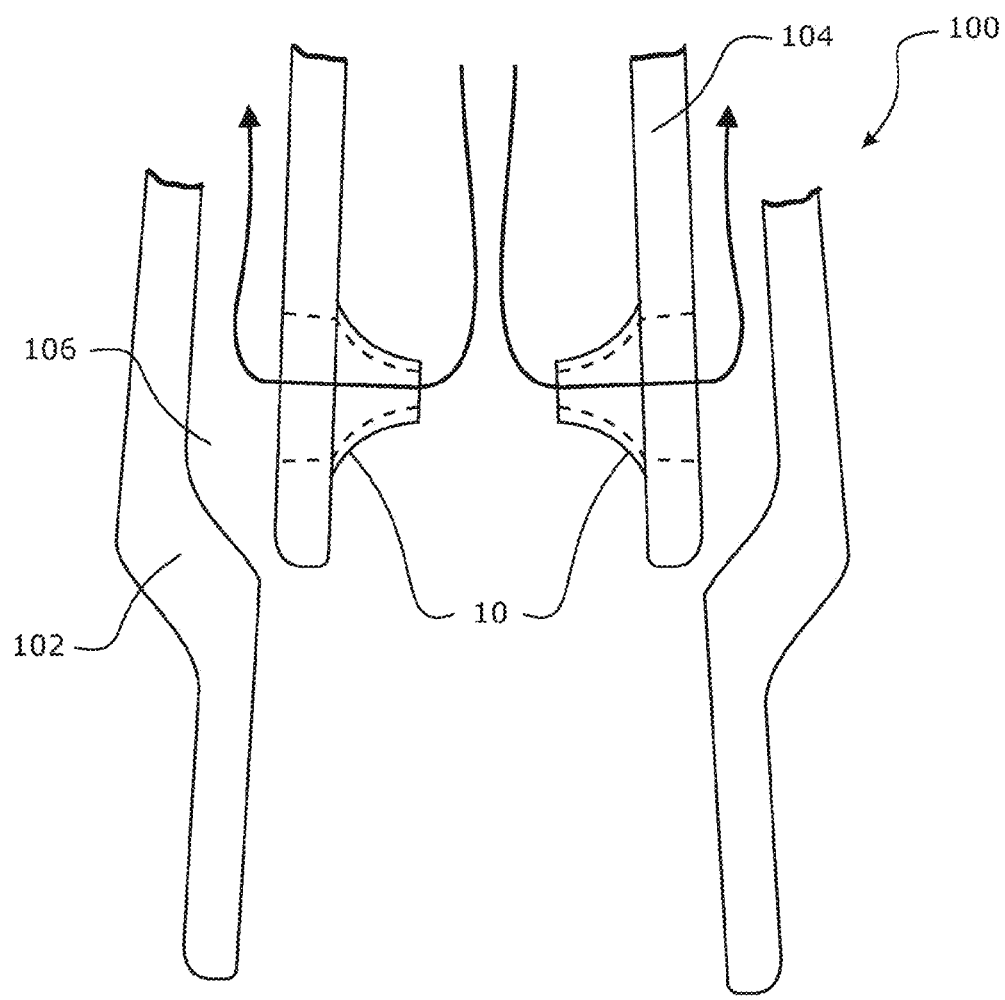

With reference now to FIG. 41, one or more valves 10 can be incorporated into a swivel connector 100. The swivel connector 100 can connect a conduit to a mask. The swivel connector 100 can include an outer flange 102. The outer flange 102 receives an inner member 104. A plenum chamber 106 can be defined between the outer flange 102 and the inner member 104. The valves 10 can be disposed around the inner member 104, for example, such that the valves direct flow into the plenum chamber 106. Other suitable configurations also can be used.

Although the present invention has been described in terms of certain embodiments, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A valve for use with system for delivering CPAP therapy, the valve comprising a base and a membrane, the membrane having a first end defining an inlet opening, the base having a second end defining an outlet opening, the first end of the membrane having at least one concave portion and at least one convex portion and the first end of the membrane being configured to collapse inwardly to vary a flow path size in response to changes in pressure acting on the membrane, wherein the valve further comprises a splint that extends into the inlet opening defined by the first end of the membrane, the splint extending from the first end of the membrane to the second end of the base, wherein the splint provides a minimum flow passage such that, if the membrane were to collapse fully around the splint, the splint would maintain a flow path.

2. The valve of claim 1, wherein the at least one concave portion and the at least one convex portion are defined by an inflection on an outer surface of the membrane.

3. The valve of claim 1, wherein the at least one concave portion and the at least one convex portion are defined by an inflection on an inner surface of the membrane.

4. The valve of claim 1, wherein the valve comprises a triangular base.

5. The valve of claim 1, wherein the valve comprises a circular base.

6. A valve assembly comprising the valve of claim 1, and a bias material disposed at the second end of the base.

7. The valve assembly of claim 6, wherein the bias material comprises a plurality of bias flow holes.

8. The valve assembly of claim 6, wherein the bias material comprises a diffuser.

9. The valve of claim 1, wherein the splint comprises a rigid tube.

10. The valve of claim 1, wherein the splint is a single tube with an inner lumen.

11. The valve of claim 1, wherein the splint comprises a plurality of posts.

12. The valve of claim 1, wherein the splint is mounted to a support structure that supports the splint in position without significantly impacting flow through the valve.

13. The valve of claim 12, wherein the support structure comprises one or more cross members.

14. The valve of claim 1, wherein the splint is supported at any location along the length of the splint.

15. The valve of claim 1, wherein one or more adjacent regions of the valve is configured to close off against an outer surface of the splint.

16. The valve of claim 1, wherein the splint comprises a same material as the rest of the valve.

17. The valve of claim 1, wherein the splint comprises a different material than the rest of the valve.

18. The valve of claim 1, wherein the splint comprises a same material as the base.

19. A valve array comprising at least two of the valves of claim 1.

20. The valve array of claim 19, wherein the at least two valves comprise two rows of valves.

21. The valve array of claim 20, wherein the two rows of valves are nested together.

\* \* \* \* \*